(12) United States Patent  (10) Patent No.: US 8,071,270 B2
Takemoto et al.  (45) Date of Patent: Dec. 6, 2011

(54) POLYHYDRIC COMPOUND AND CHEMICALLY AMPLIFIED RESIST COMPOSITION CONTAINING THE SAME

(75) Inventors: Ichiki Takemoto, Kawanishi (JP); Nobuo Ando, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 409 days.

(21) Appl. No.: 12/391,165

(22) Filed: Feb. 23, 2009

(65) Prior Publication Data

US 2009/0220886 A1  Sep. 3, 2009

(30) Foreign Application Priority Data

Feb. 22, 2008  (JP) .................. 2008-041120
Feb. 22, 2008  (JP) .................. 2008-041121

(51) Int. Cl.
*G03F 7/00*  (2006.01)
*G03F 7/004*  (2006.01)
*C07C 69/74*  (2006.01)

(52) U.S. Cl. ............. 430/270.1; 430/905; 430/910; 430/913; 430/914; 560/114; 560/116

(58) Field of Classification Search ........... 430/270.1, 430/905, 913, 914, 910; 560/114, 116
See application file for complete search history.

(56) References Cited

U.S. PATENT DOCUMENTS

| | | | | |
|---|---|---|---|---|
| 5,407,779 A | * | 4/1995 | Uetani et al. ........... | 430/192 |
| 5,866,724 A | | 2/1999 | Ichikawa et al. | |
| 6,492,085 B1 | * | 12/2002 | Shimatani et al. ....... | 430/191 |
| 6,551,755 B2 | * | 4/2003 | Hidesaka et al. ........ | 430/191 |
| 6,869,742 B2 | * | 3/2005 | Mizuta et al. .......... | 430/190 |
| 7,494,763 B2 | * | 2/2009 | Takemoto et al. ....... | 430/270.1 |
| 2008/0248417 A1 | | 10/2008 | Takemoto et al. | |

FOREIGN PATENT DOCUMENTS

JP  2006-58739 A  3/2006

OTHER PUBLICATIONS

Takemoto et. al., Molecular resists for EUV and EB Lithography, Proc. of SPIE, vol. 6923, 2008, pp. 69231N-1 to 69231N-8.

* cited by examiner

*Primary Examiner* — Amanda C. Walke
(74) *Attorney, Agent, or Firm* — Birch, Stewart, Kolasch & Birch, LLP

(57) ABSTRACT

The present invention provides a polyhydric compound represented by the formula (I):

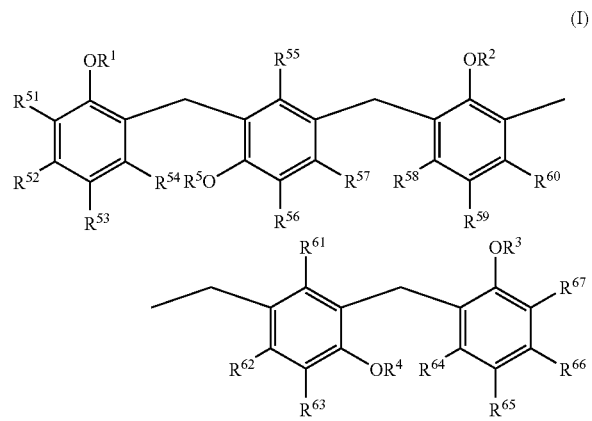

wherein $R^{51}$ to $R^{67}$ each independently represent a hydrogen atom etc., at least one selected from the group consisting of $R^1$ to $R^5$ is a group represented by the formula (II):

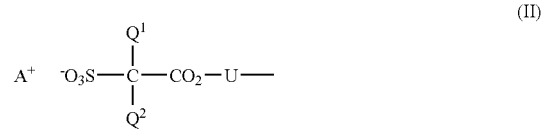

wherein $Q^1$ and $Q^2$ each independently represent a fluorine atom etc., U represents a C1-C20 divalent hydrocarbon group etc., and $A^+$ represents an organic counter ion, and the others are hydrogen atoms or groups represented by the formula (III):

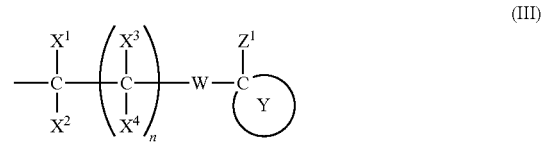

wherein $X^1$ to $X^4$ each independently represent a hydrogen atom etc., n represents an integer of 0 to 3, W represents any one of the following groups:

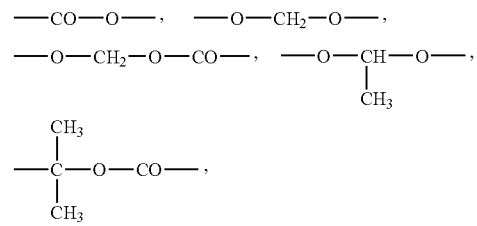

$Z^1$ represents a C1-C6 alkyl group etc., and ring Y represents a C3-C20 alicyclic hydrocarbon group, and a chemically amplified resist composition containing the same.

16 Claims, No Drawings

POLYHYDRIC COMPOUND AND CHEMICALLY AMPLIFIED RESIST COMPOSITION CONTAINING THE SAME

This nonprovisional application claims priority under 35U.S.C. §119(a) on Patent Applications No. 2008-041120 filed in JAPAN on Feb. 22, 2008 and No. 2008-041121 filed in JAPAN on Feb. 22, 2008, the entire contents of which are hereby incorporated by reference.

FIELD OF THE INVENTION

The present invention relates to a polyhydric compound and a chemically amplified resist composition containing the same.

BACKGROUND OF THE INVENTION

A chemically amplified resist composition is used for semiconductor microfabrication.

In semiconductor microfabrication, it is desirable to form patterns having high resolution, high sensitivity and good line-edge roughness, and it is expected for a chemically amplified resist composition to give such patterns.

JP 2006-58739 A discloses a chemically amplified resist composition containing a polyhydric compound wherein at least one hydroxyl group bonded to a phenyl group is protected by a 1-ethoxyethyl group.

SUMMARY OF THE INVENTION

An object of the present invention is to provide a novel polyhydric compound capable of providing a chemically amplified resist composition giving patterns having good resolution and good line edge roughness.

The other object of the present invention is to provide a chemically amplified resist composition containing the same.

These and other objects of the present invention will be apparent from the following description.

The present invention relates to the followings:

<1> A polyhydric compound represented by the formula (I):

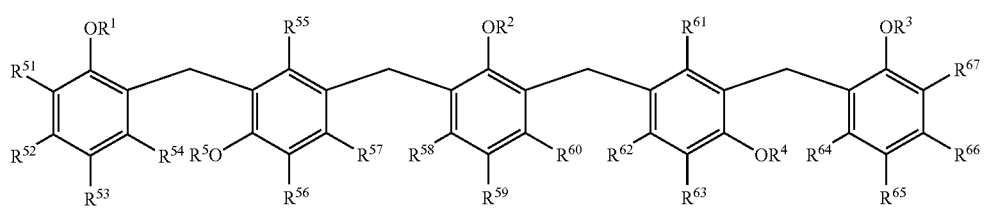

wherein $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$ and $R^{67}$ each independently represent a hydrogen atom or a C1-C4 alkyl group, at least one selected from the group consisting of $R^1$, $R^2$, $R^3$, $R^4$ and $R^5$ is a group represented by the formula (II):

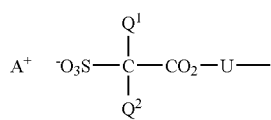

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, and $A^+$ represents an organic counter ion, and the others are hydrogen atoms or groups represented by the formula (III):

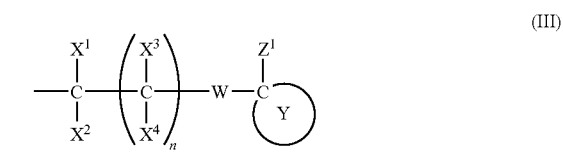

wherein $X^1$, $X^2$, $X^3$ and $X^4$ each independently represent a hydrogen atom or a C1-C4 alkyl group, n represents an integer of 0 to 3, W represents any one of the following groups:

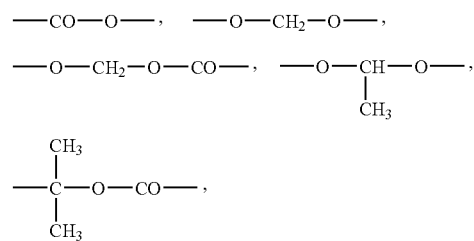

$Z^1$ represents a C1-C6 alkyl group or a C3-C12 cycloalkyl group, provided that when W is not —CO—O—, $Z^1$ may be a hydrogen atom, and ring Y represents a C3-C20 alicyclic hydrocarbon group;

<2> The polyhydric compound according to <1>, wherein at least one selected from the group consisting of $R^1$, $R^2$, $R^3$, $R^4$ and $R^5$ is a group represented by the formula (III);

<3> The polyhydric compound according to <1> or <2>, wherein $X^1$ and $X^2$ represent hydrogen atoms, n represents 0 and W is —CO—O—;

<4> The polyhydric compound according to any one of <1> to <3>, wherein $Q^1$ and $Q^2$ are fluorine atoms;

<5> The polyhydric compound according to any one of <1> to <4>, wherein the organic counter ion is at least one cation selected from the group consisting of a cation represented by the formula (VIa):

(VIa)

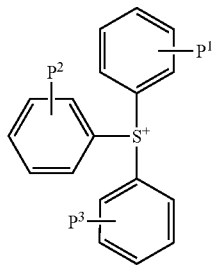

wherein P¹, P² and P³ each independently represent a hydrogen atom, a hydroxyl group, a C1-C12 alkyl group or a C1-C12 alkoxy group, a cation represented by the formula (VIb):

(VIb)

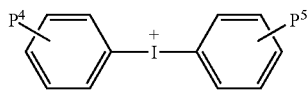

wherein P⁴ and P⁵ each independently represent a hydrogen atom, a hydroxyl group, a C1-C12 alkyl group or a C1-C12 alkoxy group, and a cation represented by the formula (VIc):

(VIc)

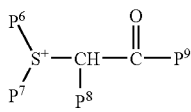

wherein P⁶ and P⁷ each independently represent a C1-C12 alkyl group or a C3-C12 cycloalkyl group, or P⁶ and P⁷ are bonded to form a C3-C12 divalent acyclic hydrocarbon group which forms a ring together with the adjacent S⁺, and at least one —CH₂— in the divalent acyclic hydrocarbon group is optionally replaced with —CO—, —O— or —S—, P⁸ represents a hydrogen atom, P⁹ represents a C1-C12 alkyl group, a C3-C12 cycloalkyl group or a C6-C10 aromatic group which may be substituted, or P⁸ and P⁹ are bonded to form a divalent hydrocarbon group which forms a 2-oxo-cycloalkyl group together with the adjacent —CHCO—, and at least one —CH₂— in the divalent hydrocarbon group may be replaced with —CO—, —O— or —S—;

<6> The polyhydric compound according to any one of <1> to <5>, wherein the molecular weight of the polyhydric compound represented by the formula (I) is 500 to 5,000;

<7> A chemically amplified resist composition comprising: the polyhydric compound represented by the formula (I) according to any one of <1> to <6> and a solvent;

<8> The composition according to <7>, wherein the composition further comprises at least one selected from the group consisting of a compound represented by the formula (I'-1):

(I'-1)

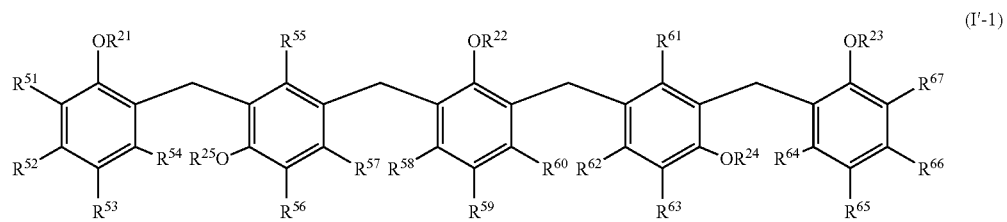

wherein $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$ and $R^{67}$ each independently represent a hydrogen atom or a C1-C4 alkyl group, and at least one selected from the group consisting of $R^{21}$, $R^{22}$, $R^{23}$, $R^{24}$ and $R^{25}$ is a group represented by the formula (III):

(III)

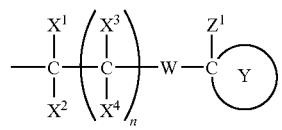

wherein X¹, X², X³ and X⁴ each independently represent a hydrogen atom or a C1-C4 alkyl group, n represents an integer of 0 to 3, W represents any one of the following groups:

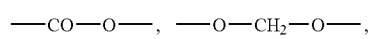

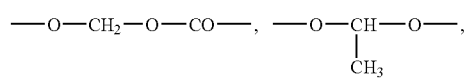

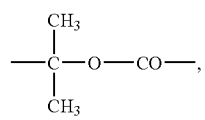

Z¹ represents a C1-C6 alkyl group or a C3-C12 cycloalkyl group, provided that when W is not —CO—O—, Z¹ may be a hydrogen atom, and ring Y represents a C3-C20 alicyclic hydrocarbon group, and the others are hydrogen atoms, a compound represented by the formula (I'-2):

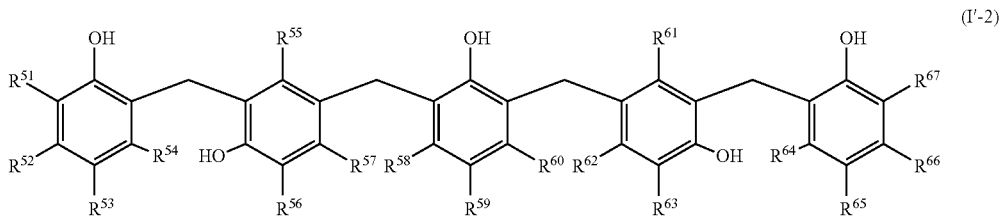

wherein $R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}$ and $R^{67}$ are the same as defined above,
a compound represented by the formula (I'-3):

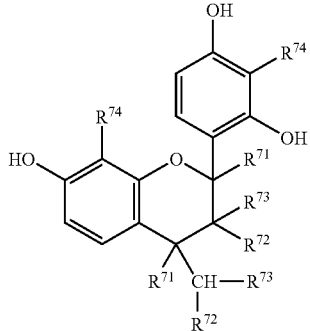

wherein $R^{71}, R^{72}$ and $R^{73}$ each independently represent a hydrogen atom, a C1-C4 alkyl group, a C2-C4 alkenyl group, a C3-C8 cycloalkyl group, a C6-C12 aryl group or a C7-C12 aralkyl group, and $R^{74}$ represents a hydrogen atom or a hydroxyl group, and a compound represented by the formula (I'-4):

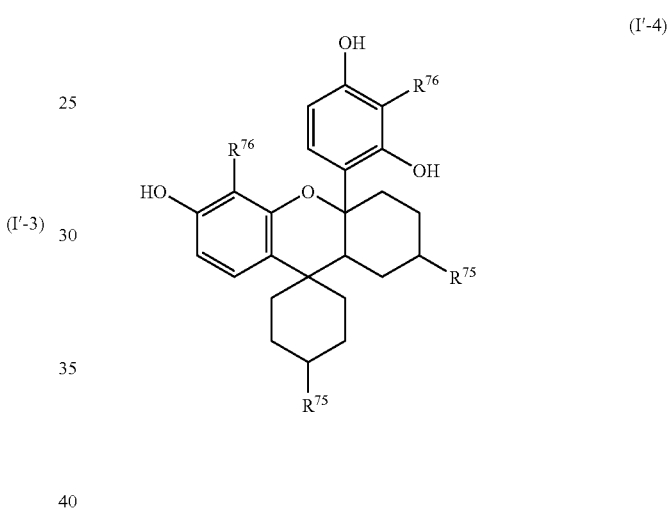

wherein $R^{75}$ represents a hydrogen atom, a C1-C4 alkyl group, a C2-C4 alkenyl group, a C3-C8 cycloalkyl group, a C6-C12 aryl group or a C7-C12 aralkyl group, and $R^{76}$ represents a hydrogen atom or a methyl group;

<9> The composition according to <7>, wherein the composition further comprises compounds represented by the formulae (I'-1) and (I'-2);

<10> The composition according to <7>, wherein the composition further comprises compounds represented by the formulae (I'-1), (I'-2) and (I'-3);

<11> The composition according to any one of <7> to <10>, wherein the composition comprises two or more kinds of a polyhydric compound represented by the formula (I);

<12> A process for producing a polyhydric compound represented by the formula (I):

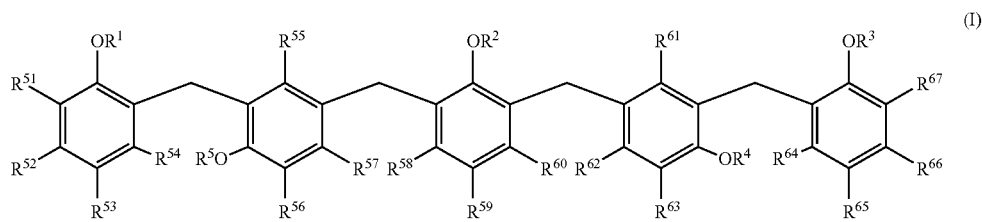

wherein $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$ and $R^{67}$ each independently represent a hydrogen atom or a C1-C4 alkyl group, at least one selected from the group consisting of $R^8$, $R^2$, $R^3$, $R^4$ and $R^5$ is a group represented by the formula (II):

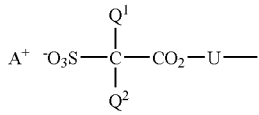
(II)

wherein $Q^1$ and $Q^2$ each independently represent a fluorine atom or a C1-C6 perfluoroalkyl group, U represents a C1-C20 divalent hydrocarbon group and $A^+$ represents an organic counter ion, and the others are hydrogen atoms or groups represented by the formula (III):

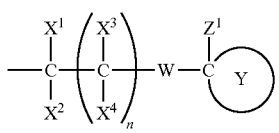
(III)

wherein $X^1$, $X^2$, $X^3$ and $X^4$ each independently represent a hydrogen atom or a C1-C4 alkyl group, n represents an integer of 0 to 3, W represents any one of the following groups:

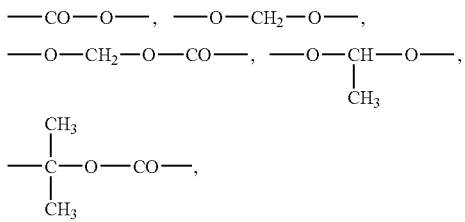

$Z^1$ represents a C1-C6 alkyl group or a C3-C12 cycloalkyl group, provided that when W is not —CO—O—, $Z^1$ may be a hydrogen atom, and ring Y represents a C3-C20 alicyclic hydrocarbon group, which comprises reacting a compound represented by the formula (VII):

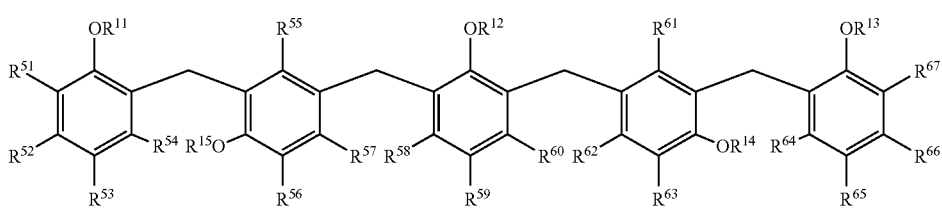
(VII)

wherein $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$ and $R^{67}$ are the same as defined above, at least one selected from the group consisting of $R^{11}$, $R^{12}$, $R^{13}$, $R^{14}$ and $R^{15}$ is a hydrogen atom and the others are hydrogen atoms or groups represented by the above-mentioned formula (III) with a compound represented by the formula (VIII):

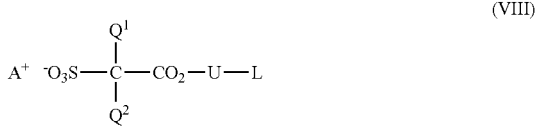
(VIII)

wherein $Q^1$, $Q^2$, U and $A^+$ are the same as defined above and L represents a halogen atom, a C1-C12 alkylsulfonyloxy group or a C6-C12 arylsulfonyloxy group wherein at least one carbon atom of the aryl group may be replaced with a hetero atom, in the presence of a base;

<13> A compound represented by the formula (VIII):

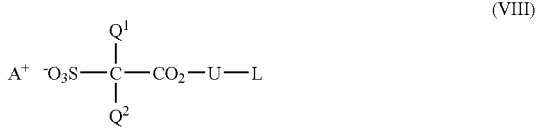
(VIII)

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, $A^+$ represents an organic counter ion, and L represents a halogen atom, a C1-C12 alkylsulfonyloxy group or a C6-C12 arylsulfonyloxy group wherein at least one carbon atom of the aryl group may be replaced with a hetero atom;

<14> A process for producing a compound represented by the formula (VIII):

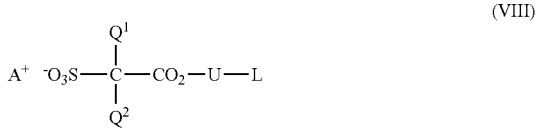
(VIII)

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, $A^+$ represents an organic counter ion, and L represents a halogen atom, a C1-C12 alkylsulfonyloxy group or a C6-C12 arylsulfonyloxy group wherein at least one carbon atom of the aryl group may be replaced with a hetero atom, which comprises reacting a compound represented by the formula (X):

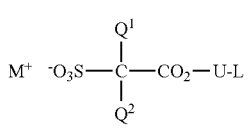 (X)

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, $M^+$ represents $Li^+$, $Na^+$, $K^+$ or $Ag^+$, and L represents a halogen atom, a C1-C12 alkylsulfonyloxy group or a C6-C12 arylsulfonyloxy group wherein at least one carbon atom of the aryl group may be replaced with a hetero atom, with a compound represented by the formula ($X^1$):

$$A^+ {}^- Z \quad (XI)$$

wherein $A^+$ is the same as defined above and $Z^-$ represents $F^-$, $Cl^-$, $Br^-$, $I^-$, $BF_4^-$, $AsF_6^-$, $SbF_6^-$, $PF_6^-$ or $ClO_4^-$;

<15> A compound represented by the formula (X):

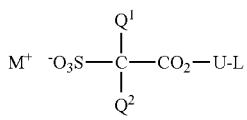 (X)

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, $M^+$ represents $Li^+$, $Na^+$, $K^+$ or $Ag^+$, and L represents a halogen atom, a C1-C12 alkylsulfonyloxy group or a C6-C12 arylsulfonyloxy group wherein at least one carbon atom of the aryl group may be replaced with a hetero atom;

<16> A process for producing a compound represented by the formula (X):

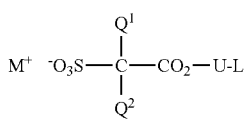 (X)

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, $M^+$ represents $Li^+$, $Na^+$, $K^+$ or $Ag^+$, and L represents a halogen atom, a C1-C12 alkylsulfonyloxy group or a C6-C12 arylsulfonyloxy group wherein at least one carbon atom of the aryl group may be replaced with a hetero atom, which comprises reacting an alcohol compound represented by the formula (XII)

$$HO-U-L \quad (XII)$$

wherein U and L are the same as defined above, with a carboxylic acid represented by the formula (XIII):

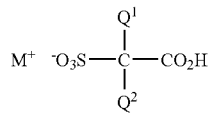 (XIII)

wherein $Q^1$, $Q^2$ and $M^+$ are the same as defined above.

DESCRIPTION OF PREFERRED EMBODIMENTS

First, the present polyhydric compound represented by the formula (I) (hereinafter, simply referred to as the polyhydric compound (I)) will be illustrated.

In the polyhydric compound (I), $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$ and $R^{67}$ each independently represent a hydrogen atom or a C1-C4 alkyl group. Examples of the C1-C4 alkyl group include a methyl group, an ethyl group, a propyl group, an isopropyl group, a butyl group, an isobutyl group and a tert-butyl group, and a methyl group is preferable.

$R^{51}$, $R^{52}$, $R^{54}$, $R^{57}$, $R^{58}$, $R^{60}$, $R^{62}$, $R^{64}$, $R^{66}$ and $R^{67}$ are preferably hydrogen atoms and $R^{53}$, $R^{55}$, $R^{56}$, $R^{59}$, $R^{61}$, $R^{63}$ and $R^{65}$ are preferably methyl groups in viewpoint of the production of the polyhydric compound (I).

In the polyhydric compound (I), at least one selected from the group consisting of $R^1$, $R^2$, $R^3$, $R^4$ and $R^5$ is a group represented by the formula (II):

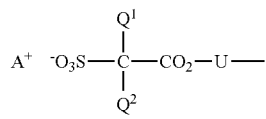 (II)

(hereinafter, simply referred to as the group (II)) and the others are hydrogen atoms or groups represented by the formula (III):

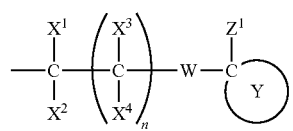 (III)

(hereinafter, simply referred to as the group (III)).

In the group (II), $Q^1$ and $Q^2$ each independently represent a fluorine atom or a C1-C6 perfluoroalkyl group. Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent the fluorine atom or the trifluoromethyl group, and $Q^1$ and $Q^2$ are more preferably the fluorine atoms.

In the group (II), U represents a C1-C20 divalent hydrocarbon group. At least one methylene group of the C1-C20 divalent hydrocarbon group may be replaced with —O—, —S—, —NH—, —CO—, —CO—O— or —NR— wherein R represents an alkyl group. Examples of the alkyl group represented by R include a C1-C4 alkyl group such as a methyl group, an ethyl group, a propyl group, an isopropyl group and a butyl group.

Examples of the C1-C20 divalent hydrocarbon group include C1-C20 linear or branched chain alkylene groups represented by the following formulae:

—CH₂—   —CH₂CH₂—   —(CH₂)₃—
—(CH₂)₄—   —(CH₂)₅—   —(CH₂)₆—
—(CH₂)₇—   —(CH₂)₈—   —(CH₂)₉—
—(CH₂)₁₀—   —(CH₂)₁₁—   —(CH₂)₁₂—
—(CH₂)₁₃—   —(CH₂)₁₄—   —(CH₂)₁₅—
—(CH₂)₁₆—   —(CH₂)₁₇—   —(CH₂)₁₈—
—(CH₂)₁₉—   —(CH₂)₂₀—   —CH(CH₃)CH₂CH₂—
—CH₂CH₂C(CH₃)₂CH₂CH₂—   —CH₂CH₂CH(C₂H₅)(CH₂)₇—
—CH₂CH₂CH(CH₃)(CH₂)₁₁—   —(CH₂)₄CH(n-C₄H₉)CH₂—
—CH(CH₃)CH(CH₃)CH(CH₃)CH(CH₃)—,

C1-C20 divalent hydrocarbon groups having a monocyclic or polycyclic structure represented by the following formulae:

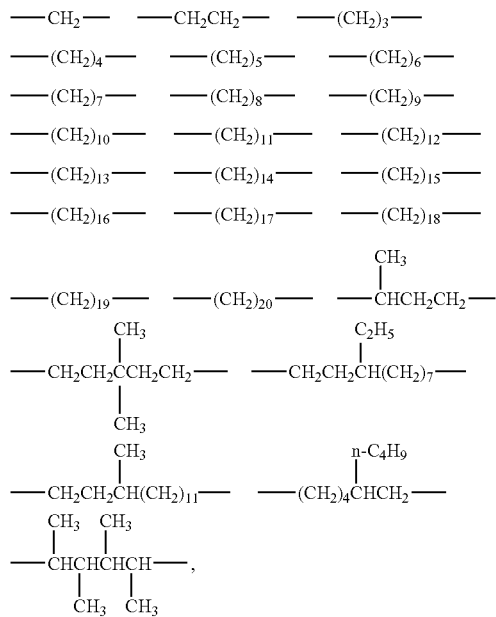

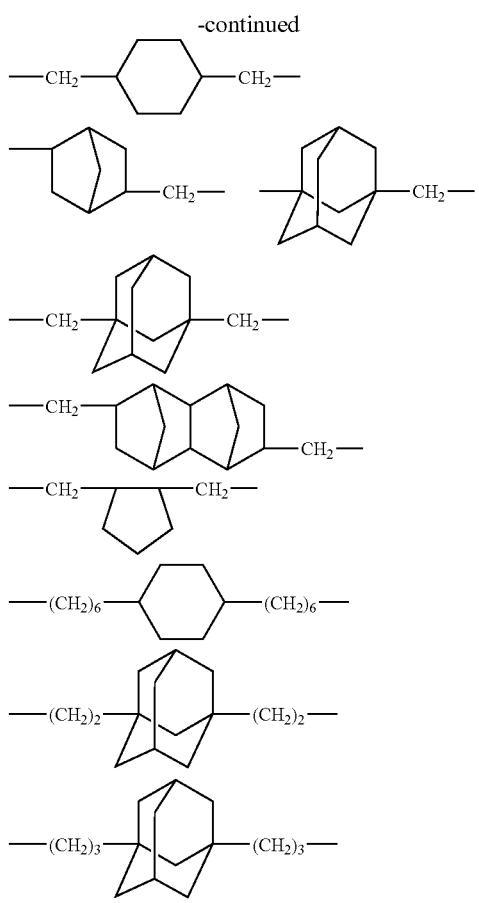

and C1-C20 divalent hydrocarbon groups of which at least one methylene group is replaced with —O—, —S—, —NH—, —CO—, —CO—O— or —NR— represented by the following formulae:

—CH₂CH₂CCH₂CH₂—   —(CH₂CH₂C)₂CH₂CH₂—
—(CH₂CH₂C)₃CH₂CH₂—   —(CH₂CH₂C)₄CH₂CH₂—
—(CH₂CH₂C)₅CH₂CH₂—   —(CH₂CH₂C)₆CH₂CH₂—
—CH₂CH₂SCH₂CH₂—
—CH₂CH₂S(CH₂CH₂S)₂CH₂CH₂—
—CH₂CH₂S(CH₂CH₂S)₄CH₂CH₂—
—CH₂CH₂CCH₂CH₂SCH₂CH₂CCH₂CH₂—
—CH₂(CH₂)₅—N(CH₃)—(CH₂)₅CH₂—
—CH₂(CH₂)₈—N(CH₃)—(CH₂)₈CH₂—
—(CH₂)₂—C(=O)—CH₂—   —(CH₂)₄—C(=O)—(CH₂)₄—
—(CH₂)₅—O—C(=O)—(CH₂)₄—
—(CH₂)₁₂—O—C(=O)—(CH₂)₄—

Among them, the C1-C20 linear or branched chain alkylene group is preferable and the C2-C16 linear or branched chain alkylene group is more preferable.

In the group (II), $A^+$ represents an organic counter ion.

Examples of the organic counter ion include a cation represented by the formula (VIa):

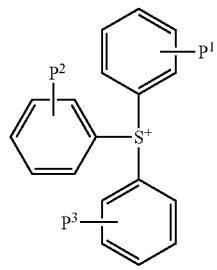

(VIa)

wherein $P^1$, $P^2$ and $P^3$ each independently represent a hydrogen atom, a hydroxyl group, a C1-C12 alkyl group or a C1-C12 alkoxy group (hereinafter, simply referred to as the cation (VIa)), a cation represented by the formula (VIb):

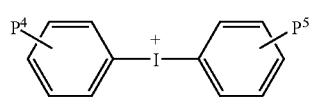

(VIb)

wherein $P^4$ and $P^5$ each independently represent a hydrogen atom, a hydroxyl group, a C1-C12 alkyl group or a C1-C12 alkoxy group (hereinafter, simply referred to as the cation (VIb)), and a cation represented by the formula (VIc):

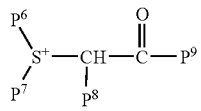

(VIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group is optionally replaced with —CO—, —O— or —S—, $P^8$ represents a hydrogen atom, $P^9$ represents a C1-C12 alkyl group, a C3-C12 cycloalkyl group or a C6-C10 aromatic group which may be substituted, or $P^8$ and $P^9$ are bonded to form a divalent hydrocarbon group which forms a 2-oxocycloalkyl group together with the adjacent —CHCO—, and at least one —$CH_2$— in the divalent hydrocarbon group may be replaced with —CO—, —O— or —S—(hereinafter, simply referred to as the cation (VIc)).

Examples of the C1-C12 alkyl group in the cations (VIa), (VIb) and (VIc) include a methyl group, an ethyl group, a propyl group, an isopropyl group, a butyl group, an isobutyl group, an sec-butyl group, a tert-butyl group, a pentyl group, a hexyl group, an octyl group and a 2-ethylhexyl group. Examples of the C1-C12 alkoxy group in the cations (VIa) and (VIb) include a methoxy group, an ethoxy group, a propoxy group, an isopropoxy group, a butoxy group, an isobutoxy group, a sec-butoxy group, a tert-butoxy group, a pentyloxy group, a hexyloxy group, an octyloxy group and a 2-ethylhexyloxy group.

Examples of the C3-C12 cycloalkyl group in the cation (VIc) include a cyclopropyl group, a cyclobutyl group, a cyclopentyl group, a cyclohexyl group, a cycloheptyl group, a cyclooctyl group and a cyclodecyl group.

Examples of the C3-C12 divalent acyclic hydrocarbon group formed by bonding $P^6$ and $P^7$ include a trimethylene group, a tetramethylene group and a pentamethylene group. Examples of the ring group formed together with the adjacent $S^+$ and the divalent acyclic hydrocarbon group include a tetramethylenesulfonio group, a pentamethylenesulfonio group and an oxybisethylenesulfonio group.

Examples of the C6-C10 aromatic group in the cation (VIc) include a phenyl group, a tolyl group, a xylyl group and a naphthyl group. Examples of the divalent hydrocarbon group formed by bonding $P^8$ and $P^9$ include a C1-C6 alkylene group such as a methylene group, an ethylene group, a trimethylene group, a tetramethylene group and a pentamethylene group, and examples of the 2-oxocycloalkyl group formed together with the adjacent —CHCO— and the divalent hydrocarbon group include a 2-oxocyclopentyl group and a 2-oxocyclohexyl group.

As the organic counter ion, the cation (VIa) is preferable and a cation represented by the formula (VId):

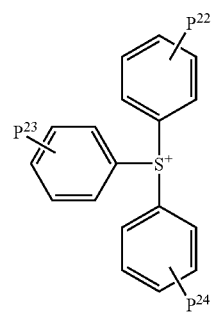

(VId)

wherein $P^{22}$, $P^{23}$ and $P^{24}$ each independently represent a hydrogen atom or a C1-C4 alkyl group, is preferable.

Examples of the C1-C4 alkyl group in the formula (VId) include a methyl group, an ethyl group, a propyl group, an isopropyl group, a butyl group, an isobutyl group, a sec-butyl group and a tert-butyl group.

Examples of the cation (VIa) include the followings:

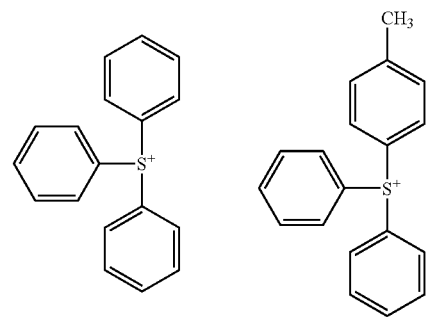

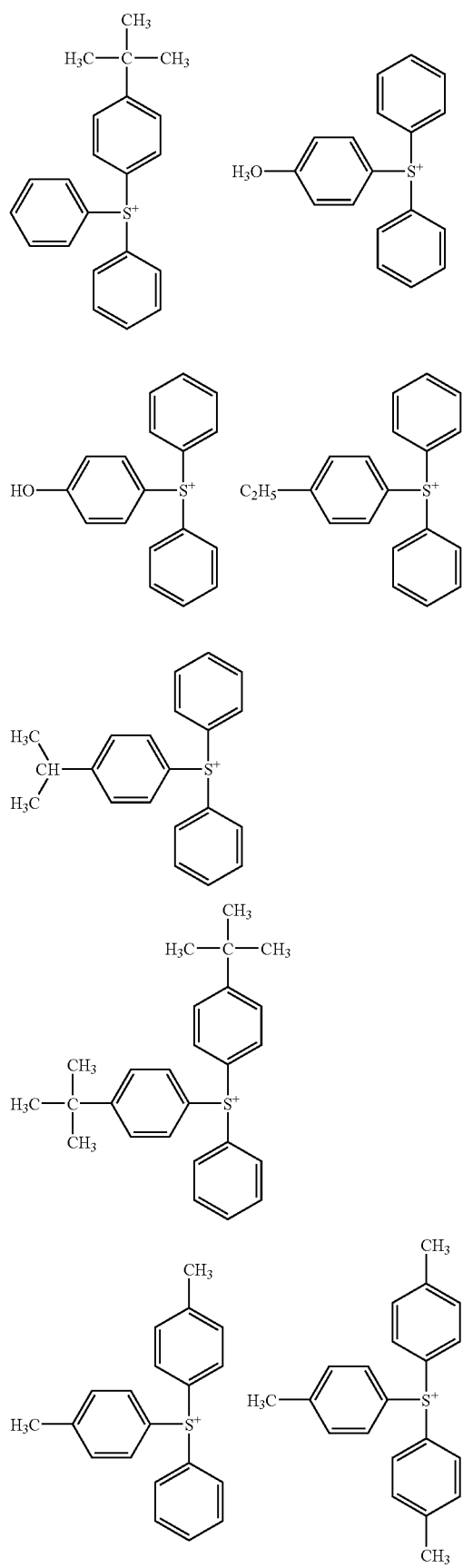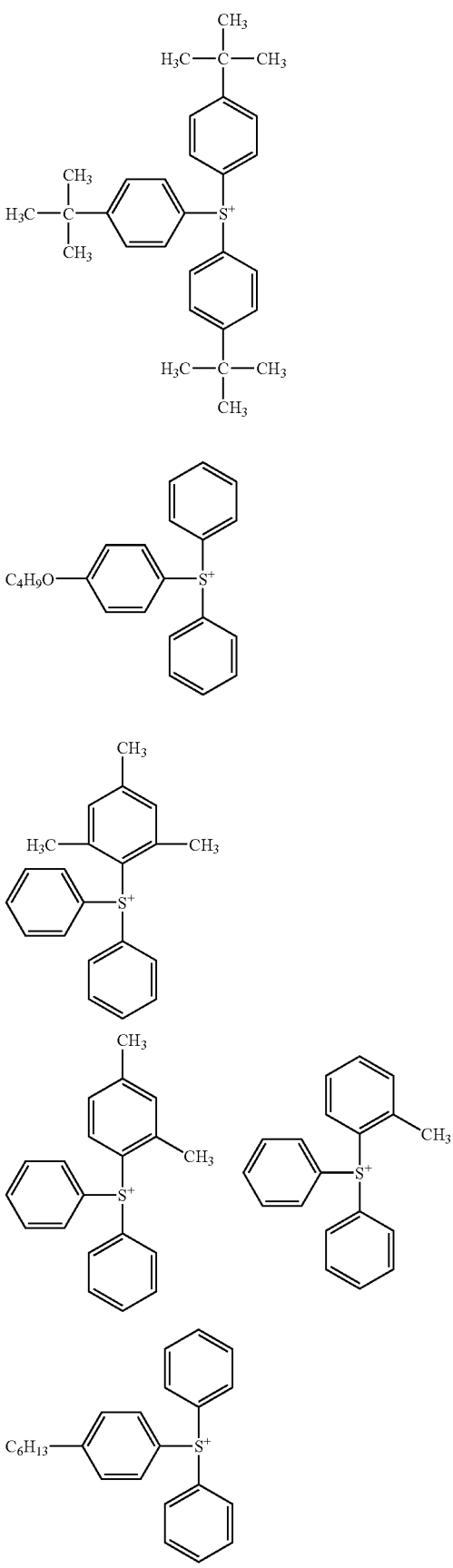

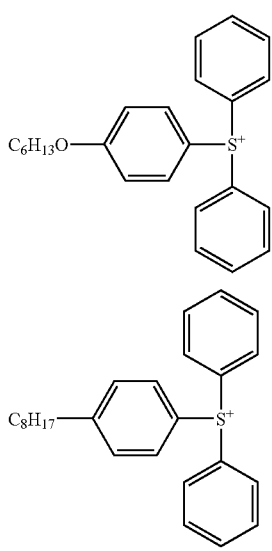
Examples of the cation (VIb) include the followings:
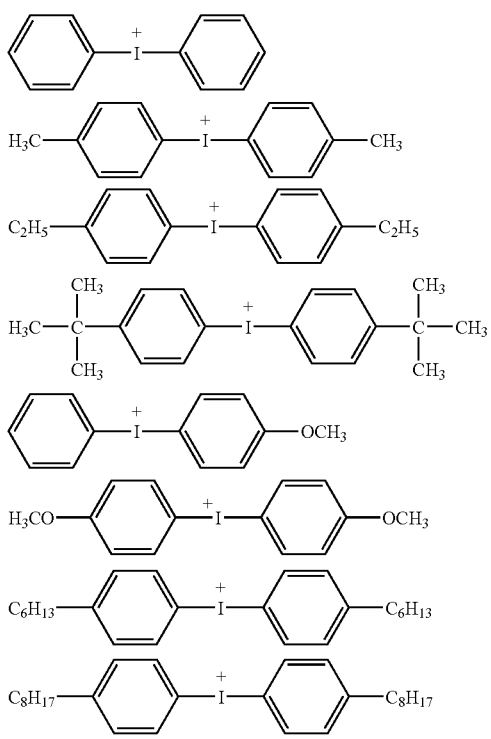
Examples of the cation (VIc) include the followings:
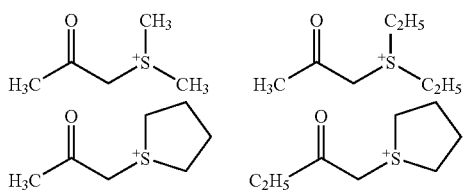
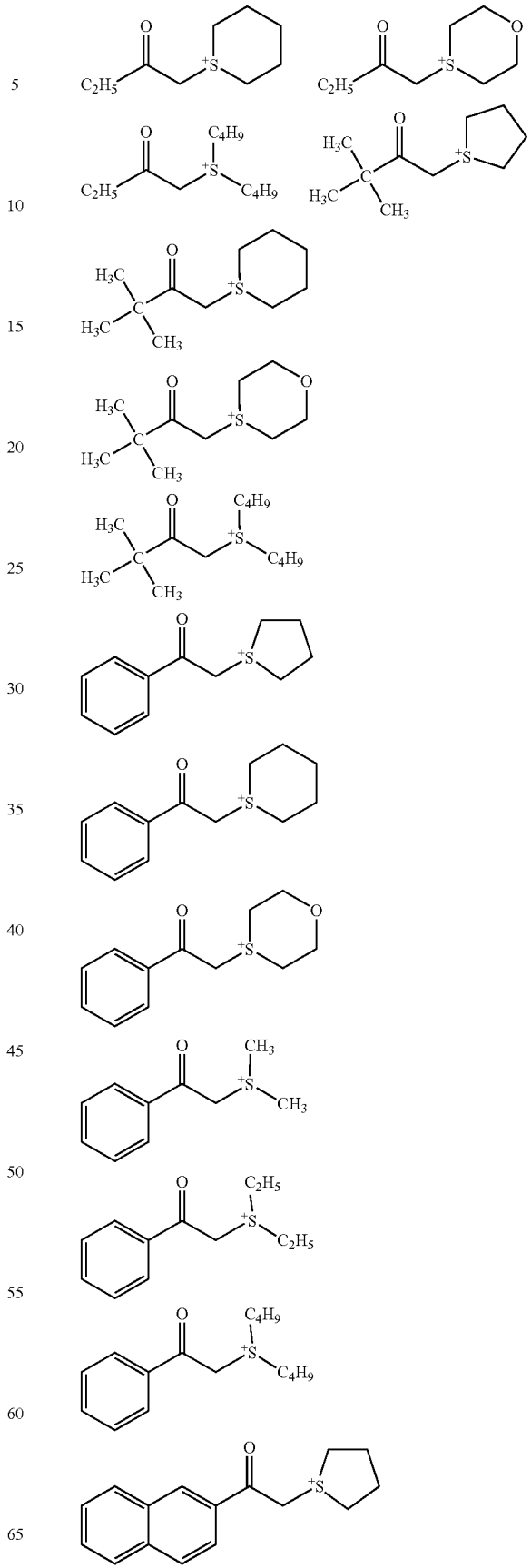

-continued
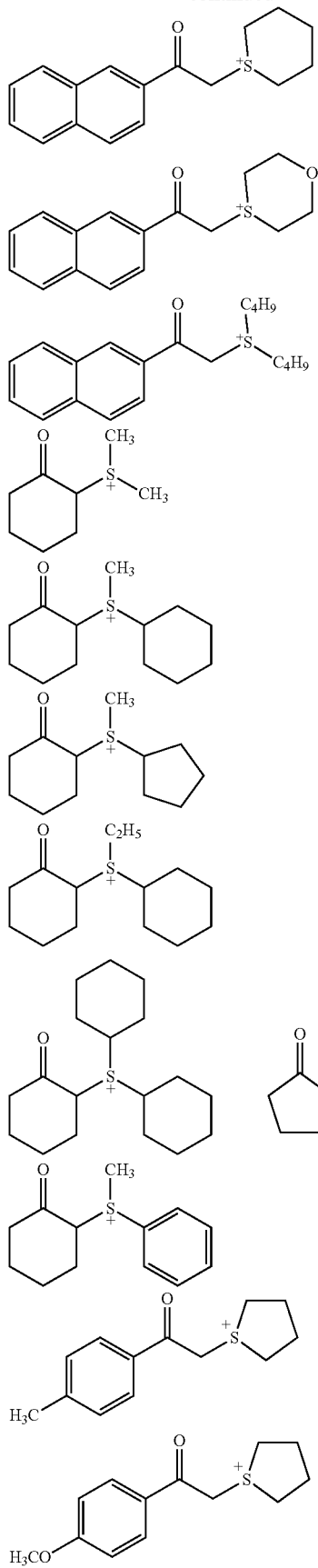
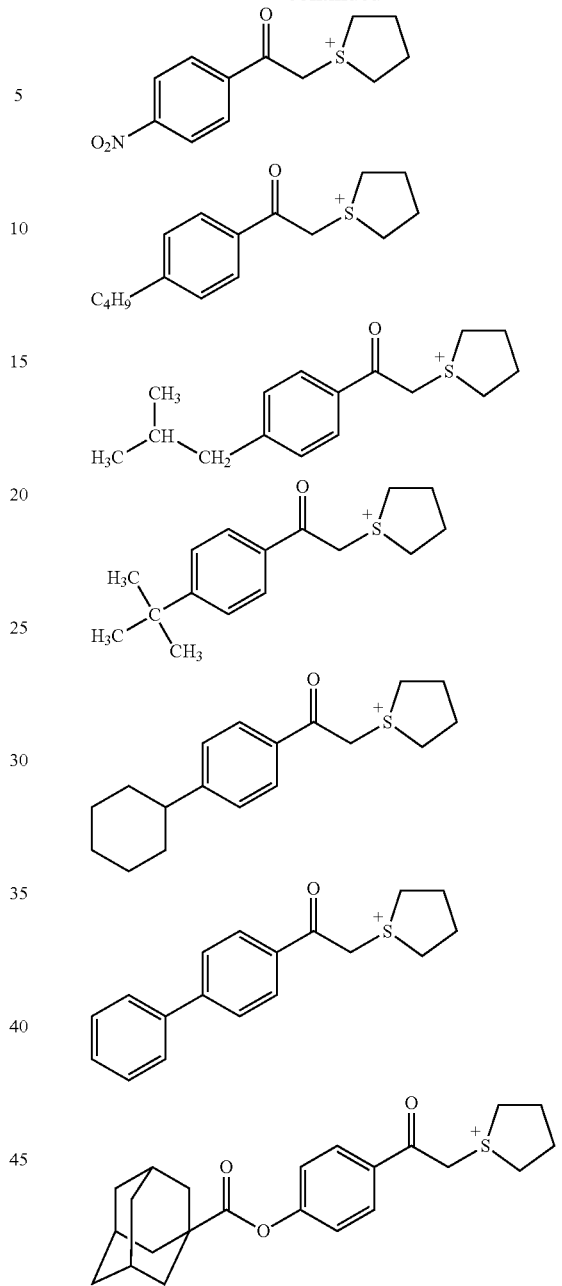
Examples of the group (II) include the groups represented by the following formulae (IIa) to (IIx).
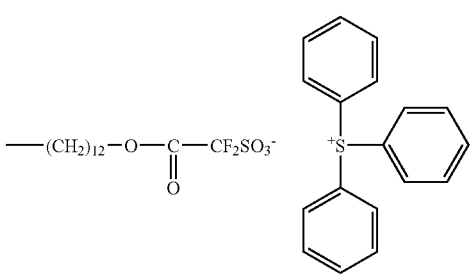
(IIa)

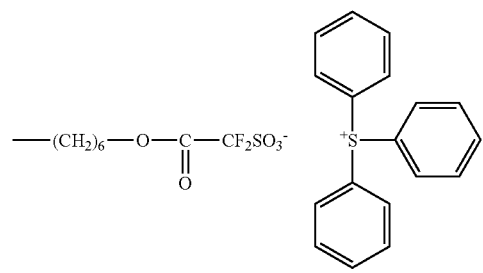 (IIb)
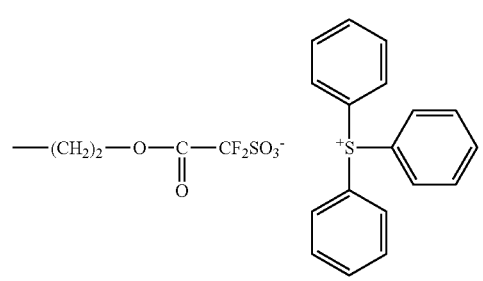 (IIc)
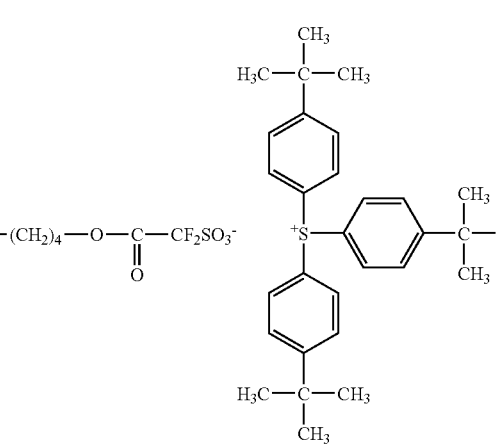 (IId)
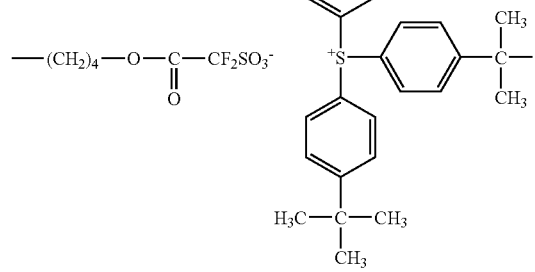 (IIe)
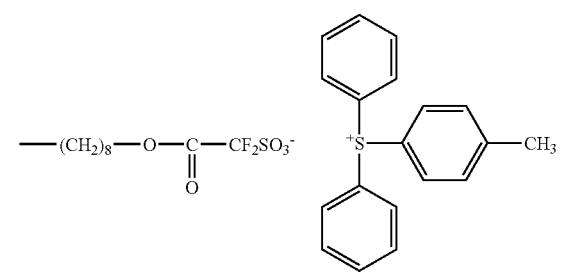 (IIf)
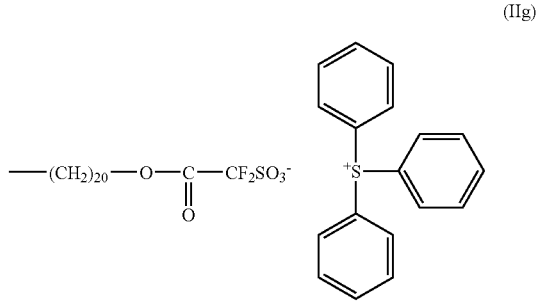 (IIg)
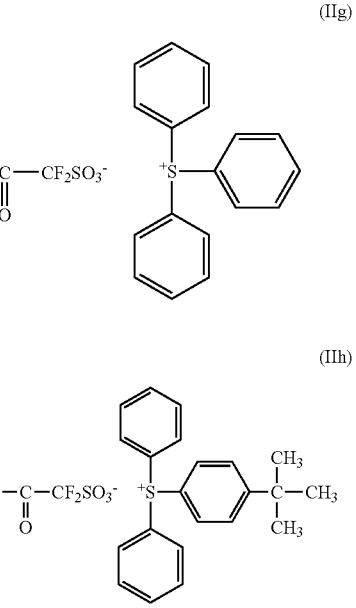
(IIh)
(IIi)
(IIj)
(IIk)
(IIm)

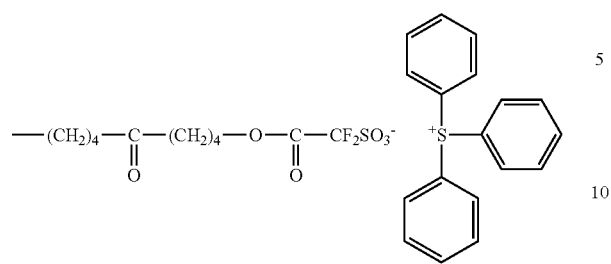
(IIn)
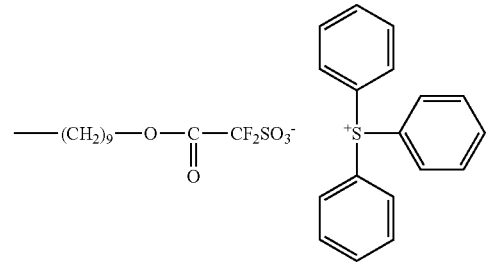
(IIs)
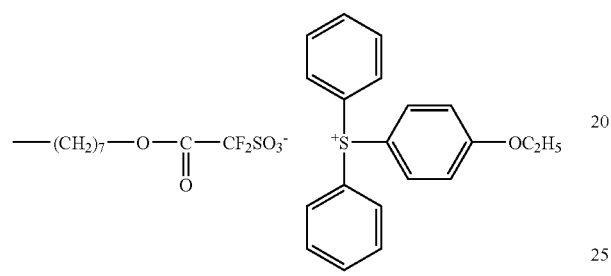
(IIo)
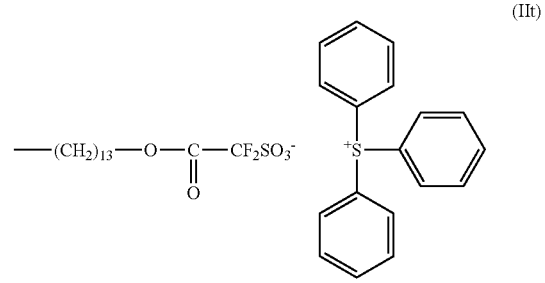
(IIt)
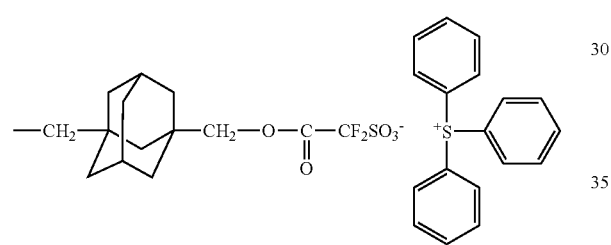
(IIp)
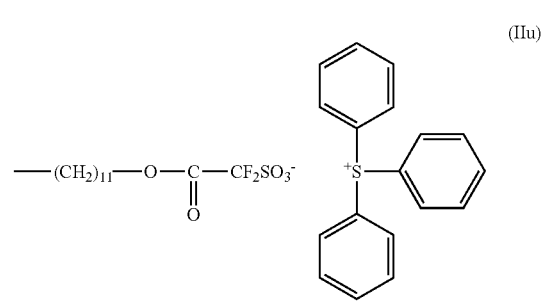
(IIu)
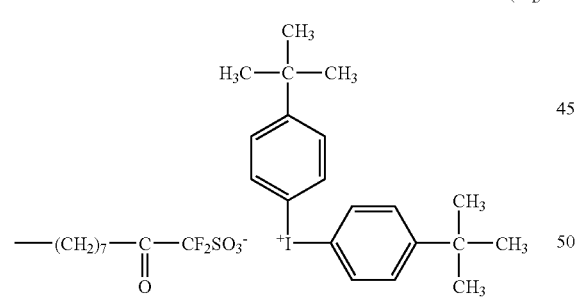
(IIq)
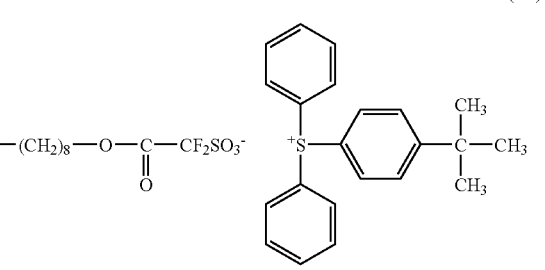
(IIv)
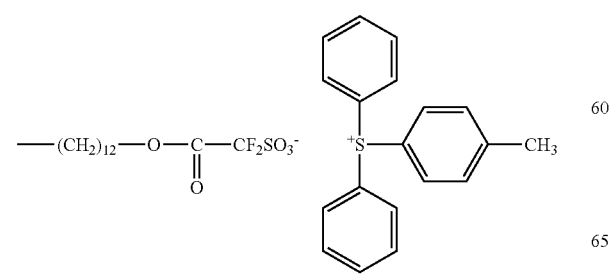
(IIr)
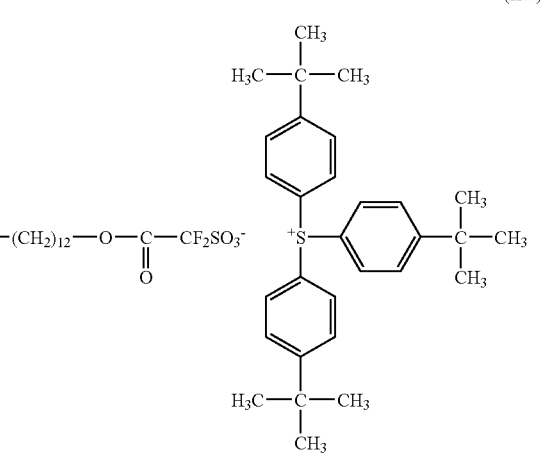
(IIw)

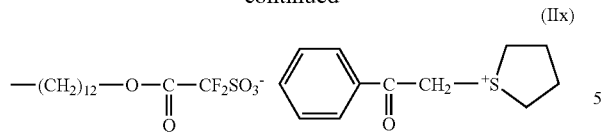
(IIx)

In the group (III), $X^1$, $X^1$, $X^3$ and $X^4$ each independently represent a hydrogen atom or a C1-C4 alkyl group. Examples of the C1-C4 alkyl group include a methyl group, an ethyl group, a propyl group, an isopropyl group, a butyl group, an isobutyl group, an sec-butyl group and a tert-butyl group. $X^1$, $X^2$, $X^3$ and $X^4$ each independently preferably represent the hydrogen atom, the methyl group or the ethyl group. $X^1$, $X^2$, $X^3$ and $X^4$ more preferably represent the same groups. All of $X^1$, $X^1$, $X^3$ and $X^4$ much more preferably represent hydrogen atoms, methyl groups or ethyl groups, and all of $X^1$, $X^2$, $X^3$ and $X^4$ especially preferably represent hydrogen atoms.

In the group (III), n represents an integer of 0 to 3, preferably an integer of 0 or 1, and more preferably 0.

W represents any one of the following groups:

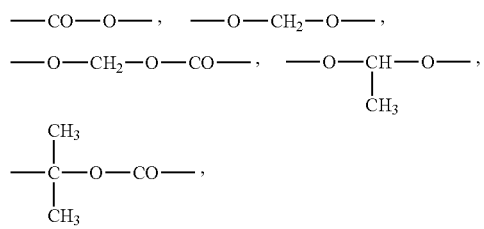

and preferably represents —CO—O—.

In the group (III), $Z^1$ represents a C1-C6 alkyl group or a C3-C12 cycloalkyl group, provided that when W is not —CO—O—, $Z^1$ may be a hydrogen atom. Examples of the C1-C6 alkyl group include a methyl group, an ethyl group, a propyl group, an isopropyl group, a butyl group, an isobutyl group, a tert-butyl group, a pentyl group, an isopentyl group and a hexyl group. Examples of the C3-C12 cycloalkyl group include a cyclopropyl group, a cyclobutyl group, a cyclopentyl group, a cyclohexyl group and a cyclooctyl group.

The ring Y represents a C3-C20 alicyclic hydrocarbon group. The alicyclic hydrocarbon group may have monocycle or bicycle or more, and the alicyclic hydrocarbon group having bicycle or more is preferable.

Examples of the C3-C20 alicyclic hydrocarbon group include the followings.

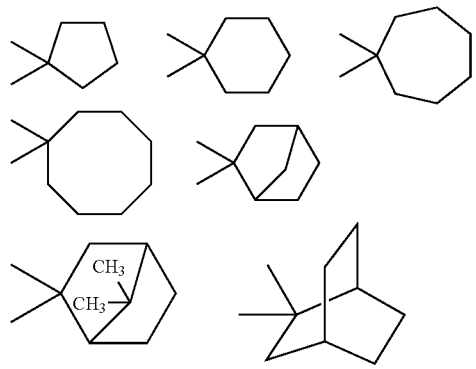

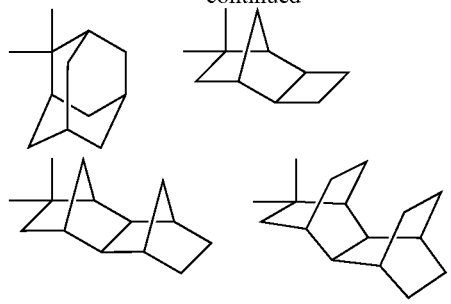

In the above formulae, one straight line with an open end shows a bond extended from the adjacent —W—, and the other straight line with an open end shows a bond extended from the adjacent group $Z^1$.

Preferable examples thereof include the followings:

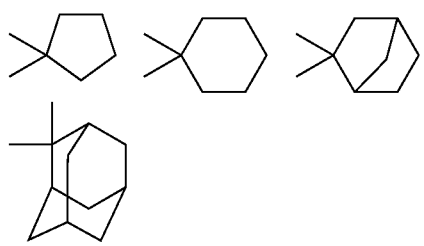

and more preferable examples thereof include the followings:

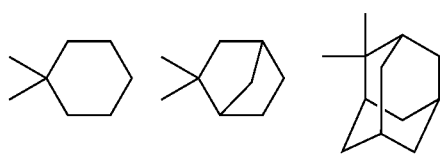

and especially preferable examples thereof include the followings:

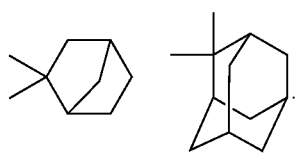

In the above formulae, one straight line with an open end shows a bond extended from the adjacent —W—, and the other straight line with an open end shows a bond extended from the adjacent group $Z^1$.

Examples of the group represented by the following formula:

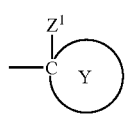

include the following groups.

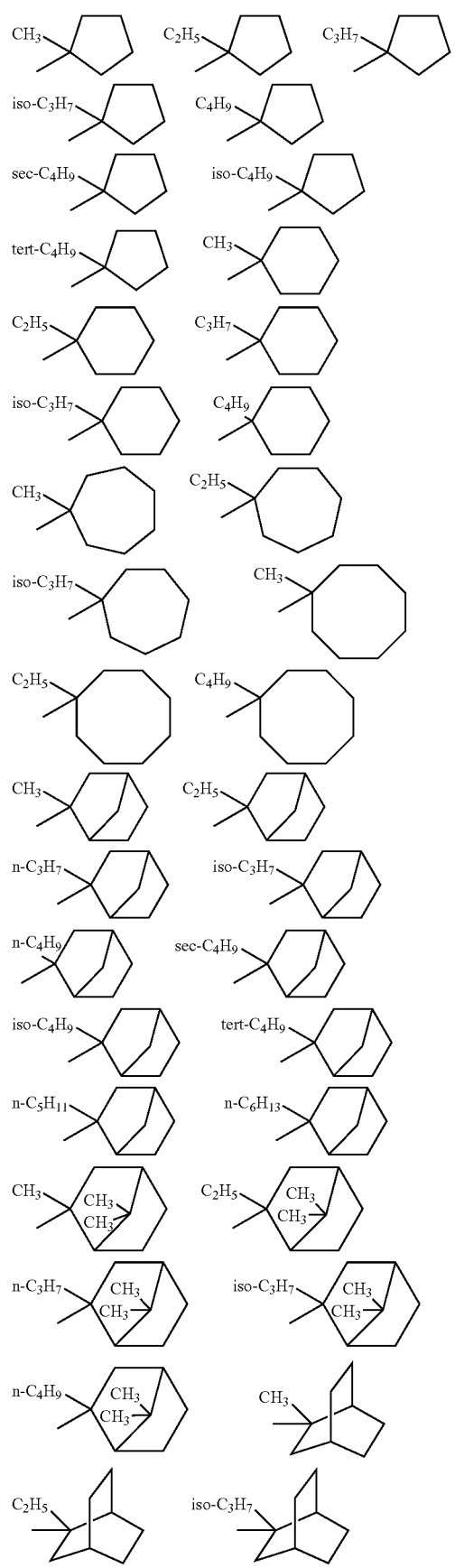
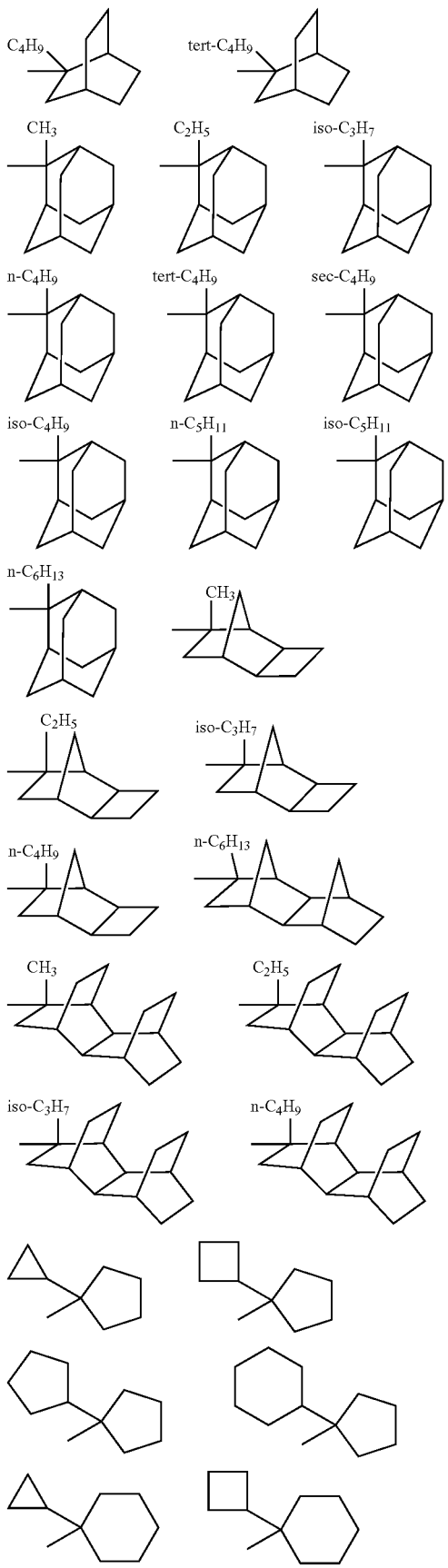

-continued

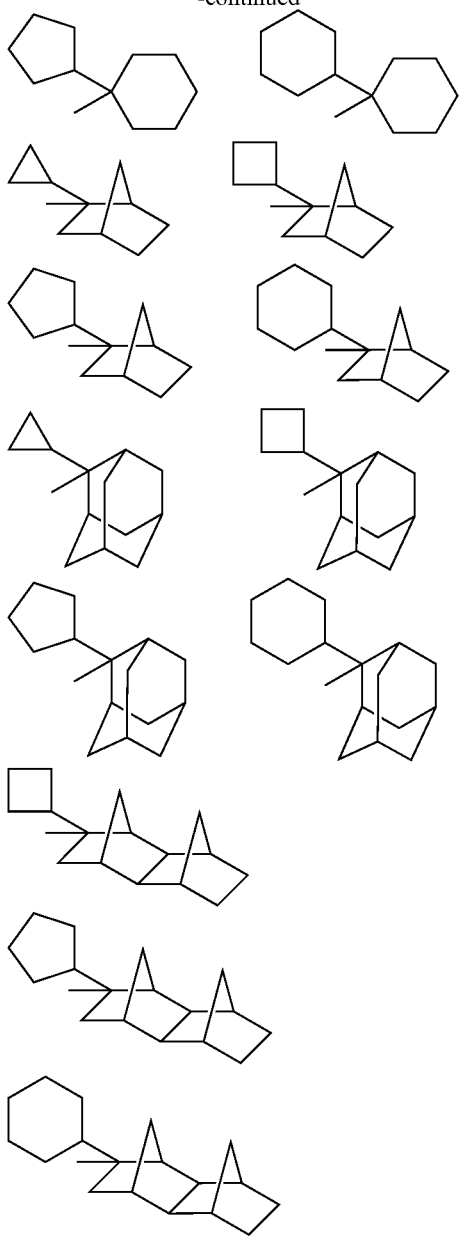
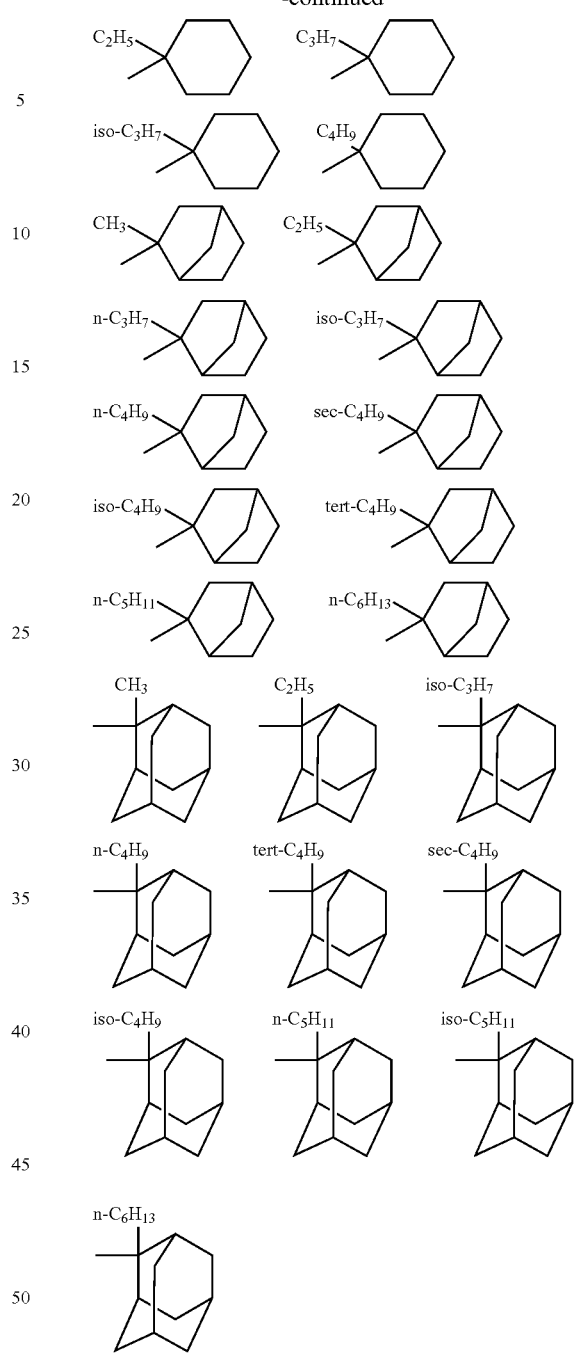

In the above formulae, a straight line with an open end shows a bond extended from the adjacent —W—.

Preferable examples thereof include

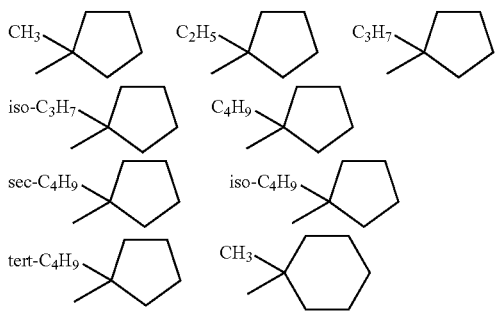

In the above formulae, a straight line with an open end shows a bond extended from the adjacent —W—.

As the group (III), the following group is preferable.

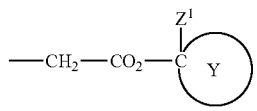

Examples of the group (III) include the groups represented by the following formulae (IIIa) to (IIIq).

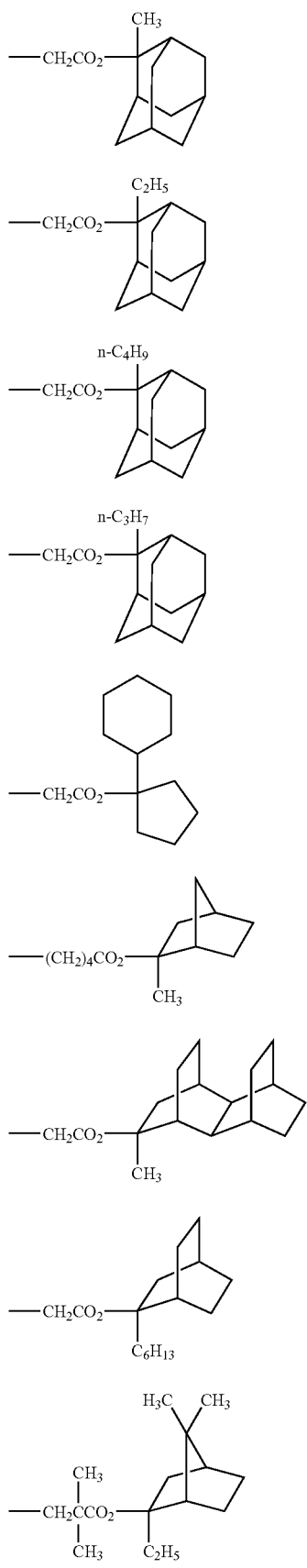
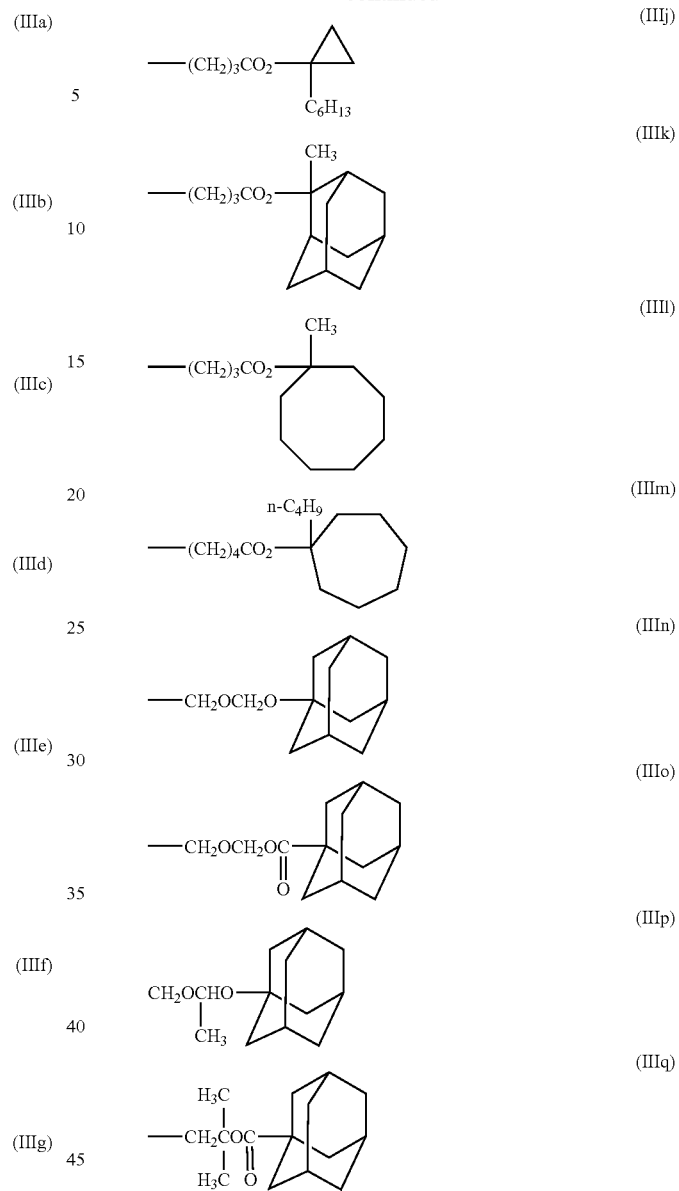

The polyhydric compound (I) wherein at least one selected from the group consisting of $R^1$, $R^2$, $R^3$, $R^4$ and $R^5$ is the group (III) is preferable.

The polyhydric compound (I) wherein one to four groups selected from the group consisting of $R^1$, $R^2$, $R^3$, $R^4$ and $R^5$ are the groups (II) is preferable, the polyhydric compound (I) wherein one to three groups selected from the group consisting of $R^1$, $R^2$, $R^3$, $R^4$ and $R^5$ are the groups (II) is more preferable.

Examples of the polyhydric compound (I) include
the polyhydric compound (I) wherein any one of $R^1$, $R^2$, $R^3$, $R^4$, and $R^5$ is the group (II), the other four groups are hydrogen atoms;
the polyhydric compound (I) wherein any one of $R^1$, $R^2$, $R^3$, $R^4$, and $R^5$ is the group (II), the other three groups are hydrogen atoms and the other one group is the group (III);
the polyhydric compound (I) wherein any one of $R^1$, $R^2$, $R^3$, $R^4$, and $R^5$ is the group (II), the other two groups are hydrogen atoms and the other two groups are the groups (III);

the polyhydric compound (I) wherein any two of $R^1$, $R^2$, $R^3$, $R^4$, and $R^4$ are the groups (II) and the other three groups are hydrogen atoms;

the polyhydric compound (I) wherein any two of $R^1$, $R^2$, $R^3$, $R^4$, and $R^5$ are the groups (II), the other two groups are hydrogen atoms and the other one group is the group (III);

the polyhydric compound (I) wherein any three of $R^1$, $R^2$, $R^3$, $R^4$, and $R^5$ are the groups (II) and the other two groups are hydrogen atoms;

the polyhydric compound (I) wherein any four of $R^1$, $R^2$, $R^3$, $R^4$, and $R^5$ are groups (II) and the other group is a hydrogen atom; and the polyhydric compound (I) wherein all of $R^1$, $R^2$, $R^3 f R^4$, and $R^5$ are the groups (II)

The molecular weight of the polyhydric compound (I) is usually 500 to 5,000, preferably 600 to 3,000 and more preferably 600 to 2,000.

Preferable examples of the polyhydric compound (I) include the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIa), the other two groups are groups represented by the above-mentioned formula (IIIa) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIa), the other two groups are groups represented by the above-mentioned formula (IIIb) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any two of $R^1$, $R^2$, $R^3$, $R^4$, and $R^5$ is the groups represented by the above-mentioned formula (IIa) and the other three groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the groups represented by the above-mentioned formula (IIa), the other one group is the groups represented by the above-mentioned formula (IIb) and the other three groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3R^4$, and $R^5$ is the groups represented by the above-mentioned formula (IIc), the other one group is the groups represented by the above-mentioned formula (IIIc) and the other three groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the groups represented by the above-mentioned formula (IId), the other two groups are the groups represented by the above-mentioned (IIIb) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIe), the other one group is the group represented by the above-mentioned formula (IIId) and the other three groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIf), the other two groups are the groups represented by the above-mentioned formula (IIIe) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any two of $R^1$, $R^2$, $R^3R^4$, and $R^5$ are the groups represented by the above-mentioned formula (IIg), the other one group is the group represented by the above-mentioned formula (IIIf) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIh), the other two groups are the groups represented by the above-mentioned formula (IIIg) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any two of $R^1$, $R^2$, $R^3$, $R^4$, and $R^5$ are the groups represented by the above-mentioned formula (IIi) and the other three groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIj), the other two groups are the groups represented by the above-mentioned formula (IIIh) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3R^4$, and $R^5$ is the group represented by the above-mentioned formula (IIk), the other one group is the group represented by the above-mentioned formula (III), the other one group is the groups represented by the above-mentioned formula (IIIi) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIm), the other two groups are the groups represented by the above-mentioned formula (IIIj) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the groups represented by the above-mentioned formula (IIn), the other two groups are the groups represented by the above-mentioned formula (IIIk) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any three of $R^1$, $R^2$, $R^3$, $R^4$, and $R^5$ are the groups represented by the above-mentioned formula (IIo) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3R^4$, and $R^5$ is the group represented by the above-mentioned formula (IIp), the other two groups are the groups represented by the above-mentioned formula (IIIl) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any two of $R^1$, $R^2$, $R^3$, $R^4$, and $R^5$ are the groups represented by the above-mentioned formula (IIq), the other one group is the group represented by the above-mentioned formula (IIIm) and the other two groups are hydrogen atoms;

the polyhydric compound (I) wherein $R^{52}$, $R^{54}$, $R^{57}$, $R^{58}$, $R^{60}$, $R^{62}$, $R^{64}$ and $R^{66}$ are hydrogen atoms, $R^{51}$, $R^{53}$, $R^{55}$, $R^{56}$, $R^{59}$, $R^{61}$, $R^{63}$, $R^{65}$ and $R^{67}$ are methyl groups, any one of $R^1$, $R^2$, $R^3$, $R^4$, and $R^5$ is the group represented by the above-mentioned formula (IIr), the other two groups are the groups represented by the above-mentioned formula (IIIa) and the other two groups are hydrogen atoms;

the polyhydric compound (I) wherein $R^{54}$, $R^{57}$ $R^{58}$, $R^{60}$, $R^{62}$, and $R^{64}$ are hydrogen atoms, $R^{51}$, $R^{52}$, $R^{53}$, $R^{55}$, $R^{56}$, $R^{61}$, $R^{63}$, $R^{65}$, $R^{66}$ and $R^{67}$ are methyl groups, $R^{59}$ is a tert-butyl group, any two of $R^1$, $R^2$, $R^3$, $R^4$, and $R^5$ are the groups represented by the above-mentioned formula (IIs) and the other three groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$ $R^4$, and $R^5$ is a group represented by the above-mentioned formula (IIt), the other two groups are groups represented by the above-mentioned formula (IIIn) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is a group represented by the above-mentioned formula (IIu), the other two groups are groups represented by the above-mentioned formula (IIIo) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is a group represented by the above-mentioned formula (IIv), the other two groups are groups represented by the above-mentioned formula (IIIp) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIr), the other two groups are groups represented by the above-mentioned formula (IIIq) and the other two groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$ $R^4$, and $R^5$ is the groups represented by the above-mentioned formula (IIw), the other one is the group represented by the above-mentioned (IIIa) and the other three groups are hydrogen atoms;

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIb), the other two groups are the groups represented by the above-mentioned (IIIa) and the other two groups are hydrogen atoms; and the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the groups represented by the above-mentioned formula (IIx), the other two groups are the groups represented by the above-mentioned (IIIb) and the other two groups are hydrogen atoms.

Next, the present chemically amplified resist composition will be illustrated.

The present resist composition contains the polyhydric compound (I) and a solvent. The present resist composition may contain two or more kinds of the polyhydric compound (I).

The polyhydric compound (I) itself is insoluble or poorly soluble in an aqueous alkali solution and becomes soluble in an aqueous alkali solution by the action of an acid. Further, the polyhydric compound (I) generates an acid by irradiation with radiation to itself or the present resist composition. The acid generated by irradiation to the present resist composition catalytically acts against the polyhydric compound (I), cleaves the group represented by the formula (II), and the polyhydric compound (I) becomes soluble in an alkali aqueous solution.

The solvent used is sufficient to dissolve the each of the components, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

Preferable examples of the present resist composition include a resist composition comprising at least one solvent selected from the group consisting of the above-mentioned solvents and at least one polyhydric compound (I) selected from the group consisting of the followings:

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is a group represented by the above-mentioned formula (IIa), the other two groups are groups represented by the above-mentioned formula (IIIa) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIa), the other two groups are groups represented by the above-mentioned formula (IIIb) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any two of $R^1$, $R^2$, $R^3$, $R^4$, and $R^5$ is the groups represented by the above-mentioned formula (IIa) and the other three groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the groups represented by the above-mentioned formula (IIa), the other one group is the groups represented by the above-mentioned formula (IIb) and the other three groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the groups represented by the above-mentioned formula (IIc), the other one group is the groups represented by the above-mentioned formula (IIIc) and the other three groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the groups represented by the above-mentioned formula (IId), the other two groups are the groups represented by the above-mentioned formula (IIIb) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is a group represented by the above-mentioned formula (IIe), the other one group is the group represented by the above-mentioned formula (IIId) and the other three groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIf), the other two groups are the groups represented by the above-mentioned formula (IIIe) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any two of $R^1$, $R^2$, $R^3$, $R^4$, and $R^5$ are the groups represented by the above-mentioned formula (IIg), the other one group is the group represented by the above-mentioned formula (IIIf) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIh), the other two groups are the groups represented by the above-mentioned formula (IIIg) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any two of $R^1$, $R^2$, $R^3$, $R^4$, and $R^5$ are the groups represented by the above-mentioned formula (IIi), and the other three groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIj), the other two groups are the groups represented by the above-mentioned formula (IIIh) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIk), the other one group is the group represented by the above-mentioned formula (III), the other one group is the groups represented by the above-mentioned formula (IIIi) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIm), the other two groups are the groups represented by the above-mentioned formula (IIIj) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the groups represented by the above-mentioned formula (IIn), the other two groups are the groups represented by the above-mentioned formula (IIIk) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any three of $R^1$, $R^2$, $R^3$, $R^4$, and $R^5$ are the groups represented by the above-mentioned formula (IIo) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is the group represented by the above-mentioned formula (IIp), the other two groups are the groups represented by the above-mentioned formula (IIIl) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any two of $R^1$, $R^2$, $R^3$, $R^4$, and $R^5$ are the groups represented by the above-mentioned formula (IIq), the other one group is the group represented by the above-mentioned formula (IIIm) and the other two groups are hydrogen atoms, the polyhydric compound (I) wherein $R^{52}$, $R^{54}$, $R^{57}$, $R^{58}$, $R^{60}$, $R^{62}$, $R^{64}$ and $R^{66}$ are hydrogen atoms, $R^{51}$, $R^{53}$, $R^{55}$, $R^{56}$, $R^{59}$, $R^{61}$, $R^{63}$, $R^{65}$ and $R^{67}$ are methyl groups, any one of $R^1$, $R^2$, $R^3$, $R^4$, and $R^5$ is the group represented by the above-mentioned formula (IIr), the other two groups are the groups represented by the above-mentioned formula (IIIa) and the other two groups are hydrogen atoms, the polyhydric compound (I) wherein $R^{54}$, $R^{57}$, $R^{58}$, $R^{60}$, $R^{62}$ and $R^{64}$ are hydrogen atoms, $R^{51}$, $R^{52}$, $R^{53}$, $R^{55}$, $R^{56}$, $R^{61}$, $R^{63}$, $R^{65}$, $R^{66}$ and $R^{67}$ are methyl groups, $R^{59}$ is a tert-butyl group, any two of $R^1$, $R^2$, $R^3$, $R^4$, and $R^5$ are the groups represented by the above-mentioned formula (IIs) and the other three groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is a group represented by the above-mentioned formula (IIt), the other two groups are groups represented by the above-mentioned formula (IIIn) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^1$, $R^2$, $R^3$, $R^4$, and $R^5$ is a group represented by the above-mentioned formula (IIu), the other two groups are groups represented by the above-mentioned formula (IIIo) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^{1}$, $R^{2}$, $R^{3}$, $R^{4}$, and $R^{5}$ is a group represented by the above-mentioned formula (IIv), the other two groups are groups represented by the above-mentioned formula (IIIp) and the other two groups are hydrogen atoms, In the present resist composition, the amount of the polyhydric compound (I) is preferably 0.1 to 60% by weight and more preferably 0.1 to 50% by weight based on the total amount of the polyhydric compound (I) and the solvent.

The present resist composition preferably contains at least one compound selected from the group consisting of a compound represented by the formula (I'-1):

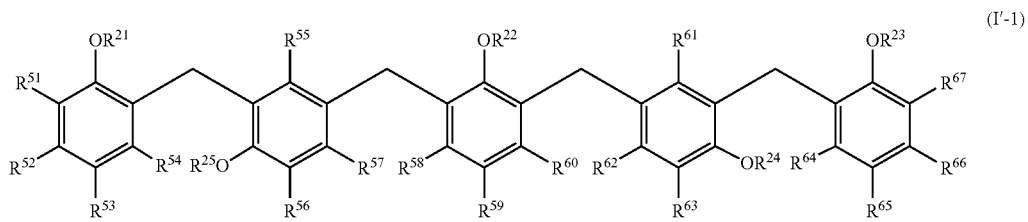
(I'-1)

the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^{1}$, $R^{2}$, $R^{3}$, $R^{4}$, and $R^{5}$ is the group represented by the above-mentioned formula (IIr), the other two groups are groups represented by the above-mentioned formula (IIIq) and the other two groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^{1}$, $R^{2}$, $R^{3}$, $R^{4}$, and $R^{5}$ is the groups represented by the above-mentioned formula (IIw), the other one is the group represented by the above-mentioned formula (IIIa) and the other three groups are hydrogen atoms, the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^{1}$, $R^{2}$, $R^{3}$, $R^{4}$, and $R^{5}$ is the group represented by the above-mentioned formula (IIb), the other two groups are the groups represented by the above-mentioned formula (IIIa) and the other two groups are hydrogen atoms and the polyhydric compound (I) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any one of $R^{1}$, $R^{2}$, $R^{3}$, $R^{4}$, and $R^{5}$ is the groups represented by the above-mentioned formula (IIx), the other two groups are the groups represented by the above-mentioned formula (IIIb) and the other two groups are hydrogen atoms.

wherein $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$ and $R^{67}$ are the same as defined above, and at least one selected from the group consisting of $R^{21}$, $R^{22}$, $R^{23}$, $R^{24}$ and $R^{25}$ is the group (III) and the others are hydrogen atoms (hereinafter, simply referred to as the compound (I'-1)), a compound represented by the formula (I'-2):

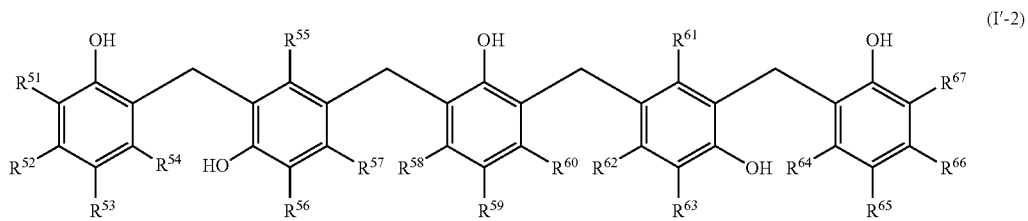
(I'-2)

wherein $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$ and $R^{67}$ are the same as defined above (hereinafter, simply referred to as the compound (I'-2)), a compound represented by the formula (I'-3):

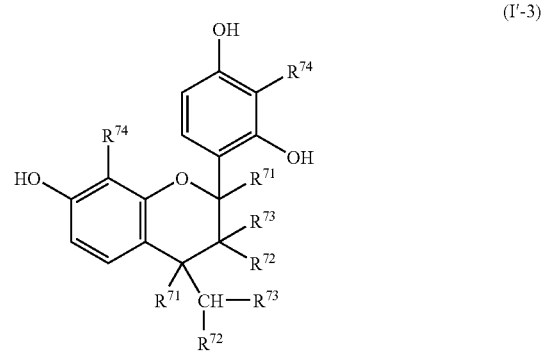
(I'-3)

wherein $R^{71}$, $R^{72}$ and $R^{73}$ each independently represent a hydrogen atom, a C1-C4 alkyl group, a C2-C4 alkenyl group, a C3-C8 cycloalkyl group, a C6-C12 aryl group or a C7-C12 aralkyl group, and $R^{74}$ represents a hydrogen atom or a hydroxyl group (hereinafter, simply referred to as the compound (I'-3)); and a compound represented by the formula (I'-4):

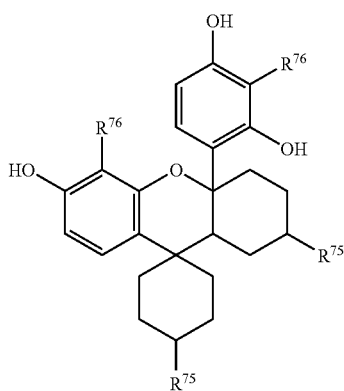

wherein $R^{75}$ represents a hydrogen atom, a C1-C4 alkyl group, a C2-C4 alkenyl group, a C3-C8 cycloalkyl group, a C6-C12 aryl group or a C7-C12 aralkyl group, and $R^{76}$ represents a hydrogen atom or a methyl group (hereinafter, simply referred to as the compound (I'-4)), in addition to the polyhydric compound (I).

The present resist composition more preferably contains at least one selected from the group consisting of the compound (I'-1) and the compound (I'-2), and especially preferably contains the compounds (I'-1) and (I'-2). The present resist composition also preferably contains the compound (I'-3) and at least one selected from the group consisting of the compound (I'-1) and the compound (I'-2).

The compound (I'-1) wherein one to three groups selected from the group consisting of $R^{21} R^{22} R^{23} R^{24}$ and $R^{25}$ are the group (III) is preferable, and the compound (I'-1) wherein two or three groups selected from the group consisting of $R^{21}$, $R^{22} R^{23}$, $R^{24}$ and $R^{25}$ are the group (III) is more preferable.

In the compound (I'-1), $R^{51}$, $R^{52}$, $R^{54}$, $R^{57}$, $R^{58}$, $R^{60}$, $R^{62}$, $R^{64}$, $R^{66}$ and $R^{67}$ are preferably hydrogen atoms, and $R^{53}$, $R^{55}$, $R^{56}$, $R^{59}$, $R^{61}$, $R^{63}$ and $R^{65}$ are preferably methyl groups.

Examples of the compound (I'-1) include the compound (I'-1) wherein $R^{51}$, $R^{52}$, $R^{54}$, $R^{57}$, $R^{58}$, $R^{60}$, $R^{62} R^{64} R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any three groups of $R^{21}$, $R^{22}$, $R^{23}$, $R^{24}$ and $R^{25}$ are the group represented by the above-mentioned formula (IIIa) and the other two groups are hydrogen atoms; the compound (I'-1) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any three groups of $R^{21}$, $R^{22}$, $R^{23}$, $R^{24}$ and $R^{25}$ are the group represented by the above-mentioned formula (IIIb) and the other two groups are hydrogen atoms; the compound (I'-1) wherein $R^5$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any two groups of $R^{21}$, $R^{22}$, $R^{23}$, $R^{24}$ and $R^{25}$ are the group represented by the above-mentioned formula (IIIa) and the other three groups are hydrogen atoms; and the compound (I'-1) wherein $R^{51}$, $R^{52}$, $R^{54}$, $R^{57}$, $R^{58}$, $R^{60}$, $R^{62}$, $R^{64}$, $R^{66}$ and $R^{67}$ are hydrogen atoms, $R^{53}$, $R^{55}$, $R^{56}$, $R^{59}$, $R^{61}$, $R^{63}$ and $R^{65}$ are methyl groups, any two groups of $R^{21}$, $R^{22}$, $R^{23}$, $R^{24}$ and $R^{25}$ are the group represented by the above-mentioned formula (IIIb) and the other three groups are hydrogen atoms.

In the compound (I'-2), $R^{51}$, $R^{52}$, $R^{54}$, $R^{57}$, $R^{58}$, $R^{60}$, $R^{62}$, $R^{64}$, $R^{66}$ and $R^{67}$ are preferably hydrogen atoms, and $R^{53}$, $R^{55}$, $R^{56}$, $R^{59}$, $R^{61}$, $R^{63}$ and $R^{65}$ are preferably methyl groups.

Examples of the compound (I'-2) include the followings.

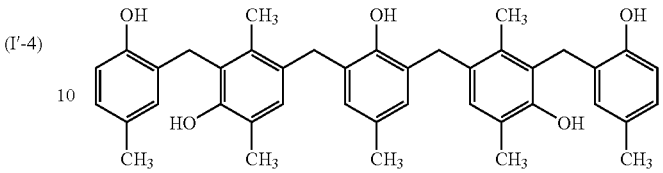

In the compounds (I'-3) and (I'-4), examples of the C1-C4 alkyl group include a methyl group, an ethyl group, a propyl group, a butyl group and an isobutyl group. Examples of the C2-C4 alkenyl group include a vinyl group, a propenyl group and a 3-butenyl group. Examples of the C3-C8 cycloalkyl group include a cyclopentyl group and a cyclohexyl group. Examples of the C6-C12 aryl group include a phenyl group and a tolyl group. Examples of the C7-C12 aralkyl group include a benzyl group. The compound (I'-3) wherein $R^{71}$, $R^{72}$ and $R^{73}$ each independently represents a hydrogen atom, a methyl group or an ethyl group is preferable. The compound (I'-4) wherein $R^{75}$ represents a hydrogen atom, a methyl group or an ethyl group is preferable.

Examples of the compounds (I'-3) and (I'-4) include the followings.

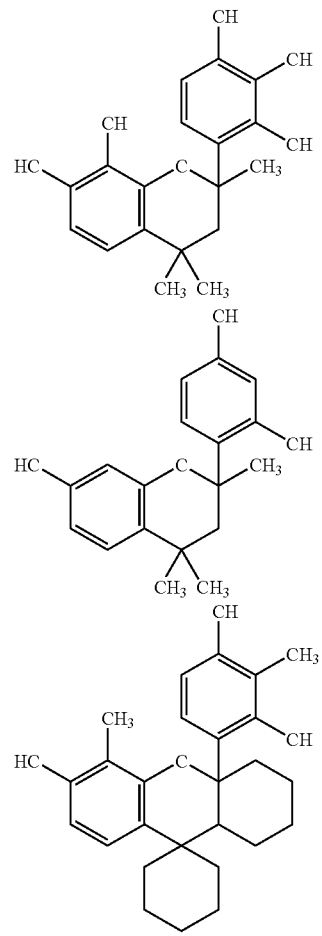

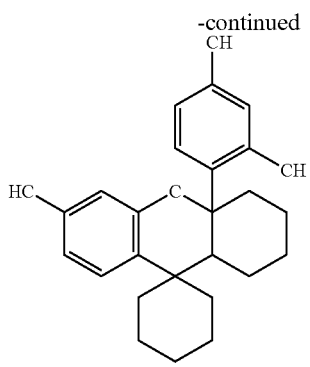

The compound (I'-3) can be produced according to the method described in U.S. Pat. No. 5,556,995. The compound (I$^{56}$-4) can be produced according to the method described in U.S. Pat. No. 5,374,742.

When the present resist composition contains at least one selected from the group consisting of the compounds (I'-1), (I'-2), (I'-3) and (I'-4) in addition to the polyhydric compound (I) and the solvent, the amount of the polyhydric compound (I) is usually 2 to 95% by weight, preferably 5 to 80% by weight and more preferably 10 to 60% by weight based on the total amount of the polyhydric compound (I), the compound (I'-1), the compound (I'-2), the compound (I'-3) and the compound (I'-4).

When the present resist composition contains the compounds (I'-1) and (I'-2) in addition to the polyhydric compound (I) and the solvent, the amount of the compound (I'-1) is usually 1 to 99% by weight based on the total amount of the compound (I'-1) and the compound (I'-2).

When the present resist composition contains the compound (I'-3) in addition to at least one selected from the group consisting of the compounds (I'-1) and (I'-2), the amount of the compound (I'-3) is usually 1 to 99% by weight based on the total amount of the compounds (I'-1), (I'-2) and (I'-3).

While the polyhydric compound (I) also acts as an acid generator in the present resist composition as described above, the present resist composition may contain the other acid generator. The acid generator can be selected from various compounds generating an acid by irradiation with radiation to the acid generator itself or a resist composition containing the acid generator. Examples of the acid generator include an onium salt, a halogenated alkyltriazine compound, a disulfone compound, a diazomethane compound having a sulfonyl group, a sulfonate compound and an imide compound having a sulfonyloxy group.

Examples of the onium salt include an onium salt in which one or more nitro groups are contained in an anion, an onium salt in which one or more ester groups are contained in an anion. Examples of the onium salt include diphenyliodonium trifluoromethanesulfonate, (4-methoxyphenyl)phenyliodonium hexafluoroantimonate, (4-methoxyphenyl)phenyliodonium trifluoromethanesulfonate, bis(4-tert-butylphenyl)iodonium tetrafluoroborate, bis(4-tert-butylphenyl)iodonium hexafluorophosphate, bis(4-tert-butylphenyl)iodonium hexafluoroantimonate, bis(4-tert-butylphenyl)iodonium trifluoromethanesulfonate, triphenylsulfonium hexafluorophosphate, triphenylsulfonium hexafluoroantimonate, triphenylsulfonium (1-adamantylmethoxy)carbonyldifluoromethanesulfonate, triphenylsulfonium (3-hydroxymethyl-1-adamantyl)methoxycarbonyldifluoromethanesulfonate, triphenylsulfonium 1-(hexahydro-2-oxo-3,5-methano-2H-cyclopenta[b]furan-6-yloxy carbonyl)difluoromethanesulfonate, triphenylsulfonium (4-oxo-1-adamantyloxy)carbonyldifluoromethanesulfonate, triphenylsulfonium (3-hydroxy-1-adamantyl)methoxycarbonyldifluoromethanesulfonate, (4-methylphenyl)diphenylsulfonium nonafluorobutanesulfonate, (4-methoxyphenyl)diphenylsulfonium hexafluoroantimonate, (4-methoxyphenyl)diphenylsulfonium trifluoromethanesulfonate, (4-methylphenyl)diphenylsulfonium trifluoromethanesulfonate, (4-methylphenyl)diphenylsulfonium heptadecafluorooctanesulfonate, (2,4,6-trimethylphenyl)diphenylsulfonium trifluoromethanesulfonate, (4-tert-butylphenyl)diphenylsulfonium trifluoromethanesulfonate, (4-phenylthiophenyl)diphenylsulfonium hexafluorophosphate, (4-phenylthiophenyl)diphenylsulfonium hexafluoroantimonate, 1-(2-naphthoylmethyl)thiolanium hexafluoroantimonate, 1-(2-naphthoylmethyl)thiolanium trifluoromethanesulfonate, (4-hydroxy-1-naphthyl)dimethylsulfonium hexafluoroantimonate and (4-hydroxy-1-naphthyl)dimethylsulfonium trifluoromethanesulfonate.

Examples of the halogenated alkyltriazine compound include
2-methyl-4,6-bis(trichloromethyl)-1,3,5-triazine,
2,4,6-tris(trichloromethyl)-1,3,5-triazine,
2-phenyl-4,6-bis(trichloromethyl)-1,3,5-triazine,
2-(4-chlorophenyl)-4,6-bis(trichloromethyl)-1,3,5-triazine,
2-(4-methoxyphenyl)-4,6-bis(trichloromethyl)-1,3,5-triazine,
2-(4-methoxy-1-naphthyl)-4,6-bis(trichloromethyl)-1,3,5-triazine,
2-(benzo[d][1,3]dioxoran-5-yl)-4,6-bis(trichloromethyl)-1,3,5-triazine,
2-(4-methoxystyryl)-4,6-bis(trichloromethyl)-1,3,5-triazine,
2-(3,4,5-trimethoxystyryl)-4,6-bis(trichloromethyl)-1,3,5-triazine,
2-(3,4-dimethoxystyryl)-4,6-bis(trichloromethyl)-1,3,5-triazine,
2-(2,4-methoxystyryl)-4,6-bis(trichloromethyl)-1,3,5-triazine,
2-(2-methoxystyryl)-4,6-bis(trichloromethyl)-1,3,5-triazine,
2-(4-butoxystyryl)-4,6-bis(trichloromethyl)-1,3,5-triazine and
2-(4-pentyloxystyryl)-4,6-bis(trichloromethyl)-1,3,5-triazine.

Examples of the sulfonate compound include 1-benzoyl-1-phenylmethyl p-toluenesulfonate (generally called "benzoin tosylate"), 2-benzoyl-2-hydroxy-2-phenylethyl p-toluenesulfonate (generally called "α-methylolbenzoin tosylate"), 1,2,3-benzene-tri-yl tris(methanesulfonate), 2,6-dinitrobenzyl p-toluenesulfonate, 2-nitrobenzyl p-toluenesulfonate and 4-nitrobenzyl p-toluenesulfonate.

Examples of the disulfone compound include diphenyl disulfone and di(p-tolyl) disulfone.

Examples of the diazomethane compound having a sulfonyl group include bis(phenylsulfonyl)diazomethane, bis(4-chlorophenylsulfonyl)diazomethane, bis(p-tolylsulfonyl)diazomethane, bis(4-tert-butylphenylsulfonyl)diazomethane, bis(2,4-xylylsulfonyl)diazomethane, bis(cyclohexylsulfonyl)diazomethane and (benzoyl)(phenylsulfonyl)diazomethane.

Examples of the imide compound having a sulfonyloxy group include N-(phenylsulfonyloxy)succinimide, N-(trifluoromethylsulfonyloxy)succinimide, N-(trifluoromethylsulfonyloxy)phthalimide, N-(trifluoromethylsulfonyloxy)-5-norbornene-2,3-dicarboxyimide, N-(trifluoromethylsulfonyloxy)naphthalimide and N-(10-camphorsulfonyloxy)naphthalimide.

The acid generator may be used alone or a mixture of two or more thereof may be used.

When the present resist composition contains the acid generator, the amount of the acid generator is usually 1 to 98% by weight, preferably 3 to 95% by weight and more preferably 5 to 80% by weight based on sum of the polyhydric compound (I) and the acid generator.

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

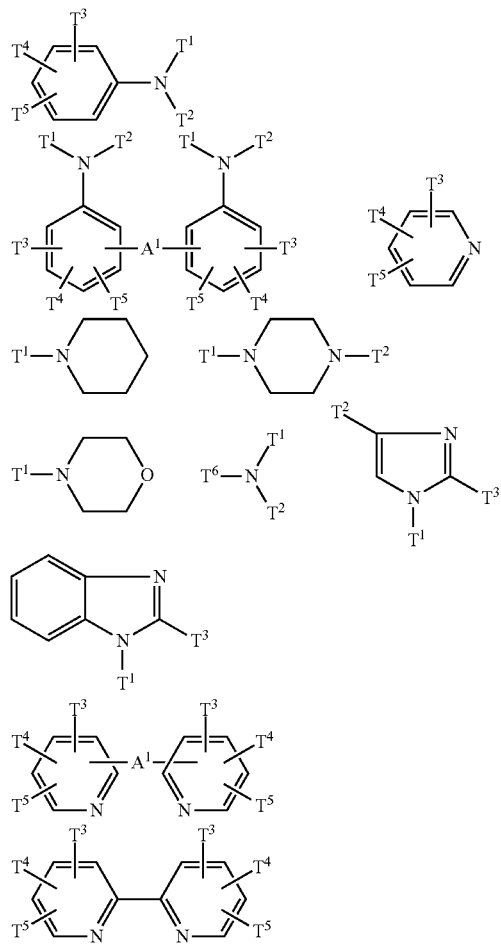

wherein $T^1$ and $T^2$ independently represent a hydrogen atom, an alkyl group, a cycloalkyl group or an aryl group, and the alkyl, cycloalkyl and aryl groups may be substituted with at least one group selected from a hydroxyl group, an amino group which may be substituted with a C1-C4 alkyl group and a C1-C6 alkoxy group which may be substituted with a C1-C6 alkoxy group, $T^3$ and $T^4$ independently represent a hydrogen atom, an alkyl group, a cycloalkyl group, an aryl group or an alkoxy group, and the alkyl, cycloalkyl, aryl and alkoxy groups may be substituted with at least one group selected from a hydroxyl group, an amino group which may be substituted with a C1-C4 alkyl group and a C1-C6 alkoxy group, or $T^3$ and $T^4$ bond together with the carbon atoms to which they bond to form an aromatic ring, $T^5$ represent a hydrogen atom, an alkyl group, a cycloalkyl group, an aryl group, an alkoxy group or a nitro group, and the alkyl, cycloalkyl, aryl and alkoxy groups may be substituted with at least one group selected from a hydroxyl group, an amino group which may be substituted with a C1-C4 alkyl group and a C1-C6 alkoxy group, $T^6$ represents an alkyl or cycloalkyl group, and the alkyl and cycloalkyl groups may be substituted with at least one group selected from a hydroxyl group, an amino group which may be substituted with a C1-C4 alkyl group and a C1-C6 alkoxy group, and $A^1$ represents —CO—, —NH—, —S—, —S—S—, an alkylene group of which at least one methylene group may be replaced with —O—, or an alkenylene group of which at least one methylene group may be replaced with —O—, and a quaternary ammonium hydroxide represented by the following formula:

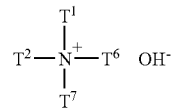

wherein $T^1$, $T^2$ and $T^6$ are the same as defined above, and $T^7$ represents a hydrogen atom, an alkyl group, a cycloalkyl group or an aryl group, and the alkyl and cycloalkyl groups may be substituted with at least one group selected from a hydroxyl group, an amino group which may be substituted with a C1-C4 alkyl group and a C1-C6 alkoxy group, and the aryl group may be substituted with at least one group selected from a hydroxyl group, an amino group which may be substituted with a C1-C4 alkyl group, a C1-C6 alkoxy group and a C1-C4 perfluoroalkyl group.

The alkyl group in $T^1$, $T^2$, $T^3$, $T^4$, $T^5$, $T^6$ and $T^7$ preferably has about 1 to 10 carbon atoms, and more preferably has about 1 to 6 carbon atoms.

Examples of the amino group which may be substituted with the C1-C4 alkyl group include an amino group, a methylamino group, an ethylamino group, an n-butylamino group, a dimethylamino group and a diethylamino group. Examples of the C1-C6 alkoxy group which may be substituted with the C1-C6 alkoxy group include a methoxy group, an ethoxy group, an n-propoxy group, an isopropoxy group, an n-butoxy group, a tert-butoxy group, an n-pentyloxy group, an n-hexyloxy group and a 2-methoxyethoxy group.

Specific examples of the alkyl group which may be substituted with at least one group selected from a hydroxyl group, an amino group which may be substituted with a C1-C4 alkyl group, and a C1-C6 alkoxy group which may be substituted with a C1-C6 alkoxy group include a methyl group, an ethyl group, an n-propyl group, an isopropyl group, an n-butyl group, a tert-butyl group, an n-pentyl group, an n-hexyl group, an n-octyl group, an n-nonyl group, an n-decyl group, a 2-(2-methoxyethoxy)ethyl group, a 2-hydroxyethyl group, a 2-hydroxypropyl group, a 2-aminoethyl group, a 4-aminobutyl group and a 6-aminohexyl group.

The cycloalkyl group in $T^1$, $T^2$, $T^3$, $T^4$, $T^5$, $T^6$ and $T^7$ preferably has about 5 to 10 carbon atoms. Specific examples of the cycloalkyl group which may be substituted with at least one group selected from a hydroxyl group, an amino group which may be substituted with a C1-C4 alkyl group and a C1-C6 alkoxy group include a cyclopentyl group, a cyclohexyl group, a cycloheptyl group and a cyclooctyl group.

The aryl group in $T^1$, $T^2$, $T^3$, $T^4$ and $T^5$ preferably has about 6 to 10 carbon atoms. Specific examples of the aryl group which may be substituted with at least one group selected from a hydroxyl group, an amino group which may be substituted with a C1-C4 alkyl group and a C1-C6 alkoxy group include a phenyl group and a naphthyl group.

The aryl group in $T^7$ preferably has about 6 to 10 carbon atoms. Specific examples of the aryl group which may be substituted with at least one group selected from a hydroxyl group, an amino group which may be substituted with a C1-C4 alkyl group, a C1-C6 alkoxy group and a C1-C4 perfluoroalkyl group include a phenyl group, a naphthyl group and a 3-trifluoromethylphenyl group.

The alkoxy group in $T^3$, $T^4$ and $T^5$ preferably has about 1 to 6 carbon atoms and specific examples thereof include a methoxy group, an ethoxy group, an n-propoxy group, an isopropoxy group, an n-butoxy group, a tert-butoxy group, an n-pentyloxy group, an n-hexyloxy group.

The alkylene and alkenylene groups in $A^1$ preferably have 2 to 6 carbon atoms. Specific examples of the alkylene group include an ethylene group, a trimethylene group, a tetramethylene group, a methylenedioxy group and an ethylene-1,2-dioxy group, and specific examples of the alkenylene group include an ethylene-1,2-diyl group, a 1-propene-1,3-diyl group and a 2-butene-1,4-diyl group.

Specific examples of the amine compound include n-hexylamine, n-heptylamine, n-octylamine, n-nonylamine, n-decylamine, aniline, 2-methylaniline, 3-methylaniline, 4-methylaniline, 4-nitroaniline, 1-naphthylamine, 2-naphthylamine, ethylenediamine, tetramethylenediamine, hexamethylendiamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptyamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecyamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher. The amount of the quencher is usually 0.001 to 10 parts by weight, preferably 0.01 to 5 parts by weight per 100 parts by weight of the polyhydric compound (I).

The present resist composition can contain, if necessary, a small amount of various additives such as a sensitizer, a solution suppressing agent, other polymers, a surfactant, a stabilizer and a dye as long as the effect of the present invention is not prevented.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

The polyhydric compound (I) can be produced by a reaction of a compound represented by the formula (VII):

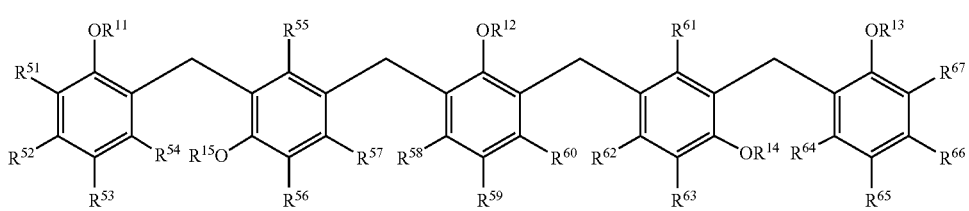

(VII)

Wherein $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$ and $R^{67}$ are the same as defined above, at least one selected from the group consisting of $R^{11}$, $R^{12}$, $R^{13}$, $R^{14}$ and $R^{15}$ is a hydrogen atom and the others are hydrogen atoms or groups (III) (hereinafter, simply referred to as the compound (VII)), with a compound represented by the formula (VIII):

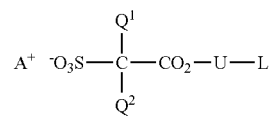

(VIII)

wherein $Q^1$, $Q^2$, U and $A^+$ are the same as defined above and L represents a halogen atom, a C1-C12 alkylsulfonyloxy group or a C6-C12 arylsulfonyloxy group wherein at least one carbon atom of the aryl group may be replaced with a hetero atom (hereinafter, simply referred to as the compound (VIII)), in the presence of a base.

Examples of the halogen atom include a fluorine atom, a chlorine atom, a bromine atom and an iodine atom. Examples of the C1-C12 alkylsulfonyloxy group include a methylsulfonyloxy group, an ethylsulfonyloxy group, an n-propylsulfonyloxy group, an isopropylsulfonyloxy group, an n-butylsulfonyloxy group, a sec-butylsulfonyloxy group, a tertbutylsulfonyloxy group, an n-pentylsulfonyloxy group, an n-hexylsulfonyloxy group, an n-heptylsulfonyloxy group, an n-octylsulfonyloxy group, an n-nonylsulfonyloxy group, an n-decylsulfonyloxy group, an n-undecylsulfonyloxy group and an n-dodecylsulfonyloxy group. Examples of the C6-C12 arylsulfonyloxy group include a phenylsulfonyloxy group and a naphthylsulfonyloxy group.

Examples of the base include an organic base such as triethylamine and pyridine; an alkali metal alkoxide such as sodium methoxide, sodium ethoxide and potassium tert-butoxide; an inorganic base such as sodium hydride, potassium carbonate and sodium hydroxide. These bases may be used alone and a mixture thereof may be used. The used amount of the base is usually 1 to 6 moles and preferably 1 to 4 moles per 1 mole of the compound (VII).

The reaction of the compound (VII) and the compound (VIII) is usually conducted in an inert solvent such as acetone, methyl ethyl ketone, toluene, tetrahydrofuran, N,N-dimethylformamide and dimethylsulfoxide. The reaction temperature is usually −30 to 200° C. and preferably 0 to 150° C.

The used amount of the compound (VIII) is usually 1 to 6 moles and preferably 1 to 4 moles per 1 mole of the compound (VII).

The reaction may be conducted in the presence of a phase transfer catalyst such as tetrabutylammonium bromide.

After completion of the reaction, the polyhydric compound (I) can be isolated, for example, by conducting extraction treatment of the reaction mixture and then concentrating the organic layer obtained. The polyhydric compound (I) isolated may be further purified by a conventional purification means such as column chromatography, recrystallization and distillation.

The compound (VII) can be produced by a reaction of the compound (I'-2) and a compound represented by the formula (IX)

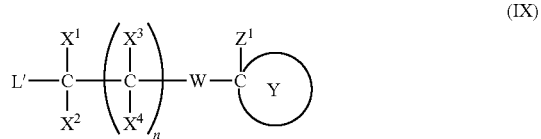

wherein $X^1$, $X^2$, $X^3$, $X^4$ n, W, $Z^1$ and Y are the same as defined above, and L' represents a chlorine atom, a bromine atom, an iodine atom, a methanesulfonyloxy group or a p-toluenesulfonyloxy group (hereinafter, simply referred to as the compound (IX)).

The compound (I'-2) can be produced according to the method described in U.S. Pat. No. 5,866,724A.

As the compound (IX), commercially available one may be used and one produced by a known method may be used.

The reaction of the compound (I'-2) and the compound (IX) is usually conducted in an inert solvent such as toluene, tetrahydrofuran, N,N-dimethylformamide and dimethylsulfoxide. The reaction temperature is usually −30 to 200° C., preferably 0 to 150° C.

The used amount of the compound (IX) is usually 1 to 6 moles, and preferably 1 to 4 moles per 1 mole of the compound (I'-2).

The reaction is preferably conducted in the presence of a base. Examples of the base include an organic base such as triethylamine and pyridine; an alkali metal alkoxide such as sodium methoxide, sodium ethoxide and potassium tert-butoxide; an inorganic base such as sodium hydride, potassium carbonate and sodium hydroxide. These bases may be used alone and a mixture thereof may be used. The amount of the base is usually 1 to 6 moles and preferably 1 to 4 moles per 1 mole of the compound (I'-2).

The reaction may be conducted in the presence of a phase transfer catalyst such as tetrabutylammonium bromide. The reaction may also be conducted in the presence of an iodide compound such as potassium iodide.

After completion of the reaction, the compound (VII) can be isolated, for example, by conducting extraction treatment of the reaction mixture and then concentrating the organic layer obtained. The compound (VII) isolated may be further purified by a conventional purification means such as column chromatography, recrystallization and distillation.

The compound (VIII) can be produced by a reaction of a compound represented by the formula (X):

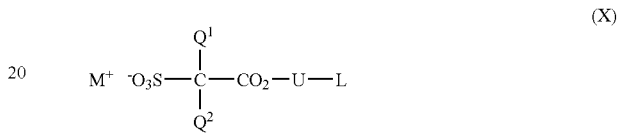

wherein $Q^1$, $Q^2$ and U are the same as defined above and $M^+$ represents $Li^+$, $Na^+$, $K^+$ or $Ag^+$ (hereinafter, simply referred to as the compound (X)) and a compound represented by the formula (XI):

wherein $A^+$ is the same as defined above and $Z^-$ represents $F^-$, $Cl^-$, $Br^-$, $I^-$, $BF_4^-$, $AsF_6^-$, $SbF_6^-$, $PF_6^-$ or $ClO_4^-$ (hereinafter, simply referred to as the compound (XI)).

The reaction of the compound (X) and the compound (XI) is usually conducted in a solvent. Examples of the solvent include an organic solvent such as chloroform, chloromethane, dichloroethane, chlorobenzene, acetone, methyl ethyl ketone, toluene, xylene, anisole, tetrahydrofuran, methanol, ethanol, isopropanol, N,N-dimethylformamide and dimethylsulfoxide; water; and a mixture thereof. The reaction temperature is usually −30 to 200° C. and preferably −10 to 100° C.

The used amount of the compound (XI) is usually 0.5 to 5 moles and preferably 1 to 2 moles per 1 mole of the compound (X).

After completion of the reaction, the compound (VIII) can be isolated, for example, by conducting extraction treatment of the reaction mixture and then concentrating the organic layer obtained. The compound (VIII) isolated may be further purified by a conventional purification means such as column chromatography, recrystallization and distillation.

The compound (X) can be produced by a reaction of an alcohol compound represented by the formula (XII):

wherein U and L are the same as defined above (hereinafter, simply referred to as the compound (XII)) and a carboxylic acid represented by the formula (XIII):

wherein $Q^1$, $Q^2$ and $M^+$ are the same as defined above (hereinafter, simply referred to as the carboxylic acid (XIII)).

The reaction of the compound (XII) and the carboxylic acid (XIII) is usually conducted in an inert solvent such as chloroform, chloromethane, dichloroethane, chlorobenzene, toluene, xylene, anisole, N,N-dimethylformamide and dimethylsulfoxide. The reaction temperature is usually −30 to 200° C. and preferably the boiling point of the used solvent to 150° C.

The used amount of the carboxylic acid (XIII) is usually 0.5 to 5 moles and preferably 0.8 to 2 moles per 1 mole of the compound (XII).

The reaction of the compound (XII) and the carboxylic acid (XIII) is preferably conducted in the presence of an acid catalyst or a dehydrating agent.

Examples of the acid catalyst include an organic acid such as methanesulfonic acid, trifluoromethanesulfonic acid, benzenesulfonic acid and p-toluenesulfonic acid; an inorganic acid such as sulfuric acid, hydrochloric acid and hydrochloride; and a strongly acidic sulfonic acid resin such as Nafion (registered trade mark). These acid catalysts may be used alone and two or more thereof may be mixed to use.

Examples of the dehydrating agent include 1,1'-carbonyldiimidazole, N,N'-dicyclohexylcarbodiimide, a 1-alkyl-2-halopyridinium salt, bis(2-oxo-3-oxazolidinyl)phosphinic chloride, 1-ethyl-3-(3-dimethylaminopropyl)carbodiimide hydrochloride, di-2-pyridyl carbonate, di-2-pyridyl thionocarbonate and 6-methyl-2-nitrobenzoic anhydride/4-(dimethylamino)pyridine.

In the case of using the acid, the reaction is preferably conducted with dehydration, for example, by Dean Stark method as the reaction time tends to be shortened.

The used amount of the acid catalyst is usually 0.001 to 3 moles and preferably 0.01 to 1 mole per 1 mole of the compound (XII).

The used amount of the dehydrating agent is usually 1 to 3 moles and preferably 1 to 2 moles per 1 mole of the compound (XII).

After completion of the reaction, the compound (X) can be isolated, for example, by concentrating or cooling the reaction mixture. The compound (X) isolated may be further purified by a conventional purification means such as column chromatography, recrystallization and distillation.

The compound (X) wherein $M^+$ is $Li^+$, $Na^+$ or $K^+$ can also be produced by reacting the compound (XII) with a carboxylic acid represented by the formula (XIV):

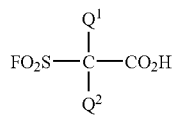

(XIV)

wherein $Q^1$ and $Q^2$ are the same as defined above (hereinafter, simply referred to as the carboxylic acid (XIV)) to obtain a compound represented by the formula (XV):

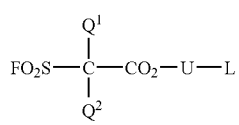

(XV)

wherein $Q^1$, $Q^2$, U and L are the same as defined above (hereinafter, simply referred to as the compound (XV)) followed by hydrolyzing the compound (XV) obtained.

The reaction of the compound (XII) and the carboxylic acid (XIV) is usually conducted according to the same manner as described in the reaction of the compound (XII) and the carboxylic acid (XIII).

The hydrolysis reaction of the compound (XV) is usually conducted in an inert solvent such as chloroform, chloromethane, dichloroethane, chlorobenzene, acetone, methyl ethyl ketone, toluene, xylene, anisole, tetrahydrofuran, N,N-dimethylformamide and dimethylsulfoxide using an inorganic base such as lithium hydroxide, sodium hydroxide, potassium hydroxide, sodium carbonate, potassium carbonate, sodium hydrogen carbonate and potassium hydrogen carbonate. The reaction temperature is usually −30 to 200° C. and preferably −10 to 150° C. The used amount of the inorganic base is usually 1 to 5 moles and preferably 1 to 2 moles per 1 mole of the compound (XV). The compound (X) wherein $M^+$ is $Ag^+$ can be produced by reacting the obtained compound (X) wherein $M^+$ is $Li^+$, $Na^+$ or $K^+$ with silver nitrate.

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be described more specifically by Examples, which are not construed to limit the scope of the present invention.

EXAMPLE 1

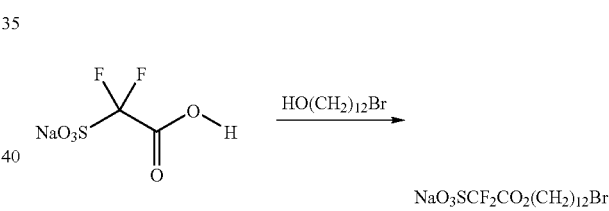

(A)

(1) Three hundred grams of toluene, 21g of sodium salt of difluorosulfoacetic acid, 25g of 12-bromo-1-dodecanol and catalytic amounts of p-toluenesulfonic acid were mixed. The mixture obtained was refluxed for 13 hours to conduct a dehydration reaction. The mixture was cooled and then, the precipitates were collected by filtration. The precipitates were washed with a little amount of toluene and dried to obtain 34.1 g of sodium salt of 12-bromo-1-dodecyl difluorosulfoacetate. Yield: 81.2%.

$^1$H-NMR (CDCl$_3$, Internal standard: tetramethylsilane): δ (ppm) 4.33 (t, 2H, J=6.9 Hz), 3.40 (t, 2H, J=6.9 Hz), 1.85 (m, 2H), 1.78-1.10 (m, 18H)

MS (ESI(−) Spectrum): M$^-$ 421 (C$_{14}$H$_{24}$BrF$_2$O$_5$S$^-$=421.05)

(2) To 200g of chloroform, 34.1 g of sodium salt of 12-bromo-1-dodecyl difluorosulfoacetate was added. To the obtained solution, 192g of 13.1% by weight of aqueous triphenylsulfonium chloride solution was added and the resultant mixture was stirred over night. The mixture was separated to obtain the aqueous layer and the organic layer. The organic later obtained was washed with an ion-exchanged water. The organic layer was concentrated to obtain 48.7 g of the salt represented by the above-mentioned formula (A), which is called as SALT (A). Yield: 92.7%.

$^1$H-NMR (dimethylsulfoxide-d$_6$, Internal standard: tetramethylsilane): δ (ppm) 7.87-7.76 (m, 15H), 4.17 (t, 2H, J=6.9 Hz), 3.50 (t, 2H, J=6.9 Hz), 1.75 (m, 2H), 1.57 (m, 2H), 1.37-1.23 (m, 16H)

$^{19}$F-NMR (dimethylsulfoxide-d$_6$, Internal standard: fluorobenzene): δ (ppm)-105.19

MS (ESI(+) Spectrum): M$^+$ 263 (C$_{18}$H$_{15}$S$^+$=263.09)

MS (ESI(−) Spectrum): M$^-$ 421 (C$_{14}$H$_{24}$BrF$_2$O$_5$S$^2$=421.05)

EXAMPLE 2

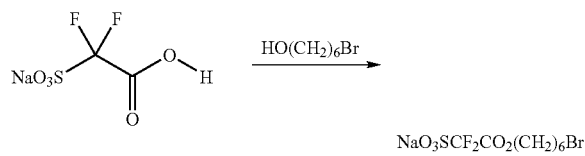

NaO$_3$SCF$_2$CO$_2$(CH$_2$)$_6$Br

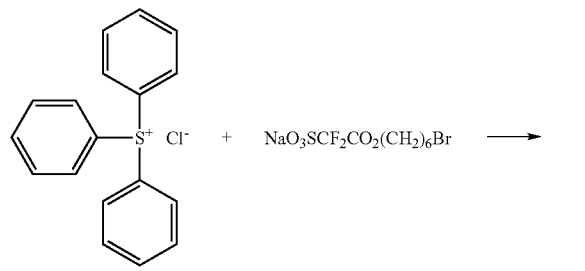

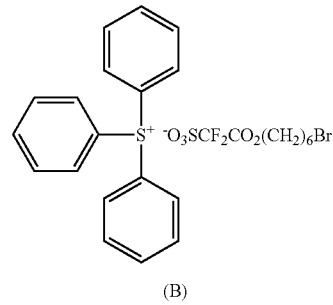

(B)

(1) Fifty grams of toluene, 10g of sodium salt of difluorosulfoacetic acid, 10.8 g of 6-bromo-1-hexanol and catalytic amounts of trifluoromethanesulfonic acid were mixed. The mixture obtained was refluxed for 9 hours to conduct a dehydration reaction. The mixture was cooled and then, the precipitates were collected by filtration. The precipitates were washed with a little amount of toluene and dried to obtain 12.3 g of sodium salt of 6-bromo-1-hexyl difluorosulfoacetate. Yield: 72.0%.

$^1$H-NMR (CDCl$_3$, Internal standard: tetramethylsilane): δ (ppm) 4.35 (t, 2H, J=6.9 Hz), 3.42 (t, 2H, J=6.9 Hz), 1.86 (m, 2H) 1.73 (m, 2H), 1.47 (m, 2H), 1.40 (m, 2H)

MS (ESI(−) Spectrum): M$^-$ 337 (C$_8$H$_{12}$BrF$_2$O$_5$S$^-$=336.96)

(2) To 200g of chloroform, 12.1 g of sodium salt of 6-bromo-1-hexyl difluorosulfoacetate was added. To the obtained solution, 84.1 g of 13.1% by weight of aqueous triphenylsulfonium chloride solution was added and the resultant mixture was stirred over night. The mixture was separated to obtain the aqueous layer and the organic layer. The organic later obtained was washed with an ion-exchanged water. The organic layer was concentrated to obtain 17.2 g of the salt represented by the above-mentioned formula (B), which is called as SALT (B). Yield: 85.3%.

$^1$H-NMR (dimethylsulfoxide-d$_6$, Internal standard: tetramethylsilane): δ (ppm) 7.77-7.68 (m, 15H), 4.25 (t, 2H, J=6.9 Hz), 3.37 (t, 2H, J=6.9 Hz), 1.81 (m, 2H), 1.70 (m, 2H), 1.45-1.36 (m, 4H)

$^{19}$F-NMR (dimethylsulfoxide-d$_6$, Internal standard: fluorobenzene): δ (ppm)-106.42

MS (ESI(+) Spectrum): M$^+$ 263 (C$_{18}$H$_{15}$S$^+$=263.09)

MS (ESI(−) Spectrum): M$^-$ 337 (C$_8$H$_{12}$BrF$_2$O$_5$S$^{2-}$2=336.96)

EXAMPLE 3

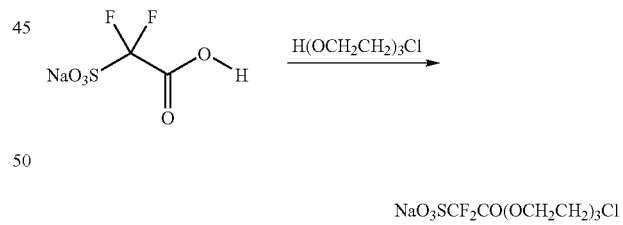

NaO$_3$SCF$_2$CO(OCH$_2$CH$_2$)$_3$Cl

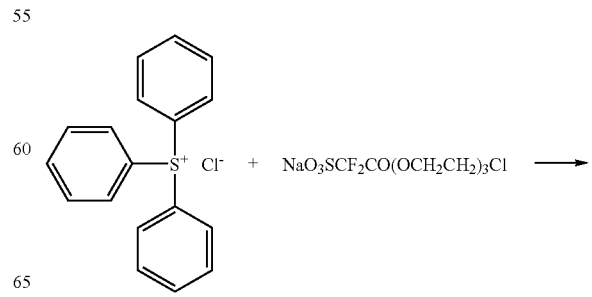

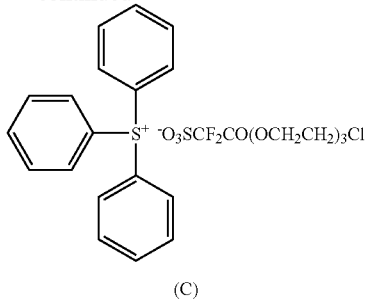

(C)

(1) Fifty grams of toluene, 10g of sodium salt of difluorosulfoacetic acid, 7.5 g of 2-[2-(2-chloroethoxy)ethoxy]ethanol and catalytic amounts of trifluoromethanesulfonic acid were mixed. The mixture obtained was refluxed for 10 hours to conduct a dehydration reaction. The mixture was concentrated to obtain 17.8 g of sodium salt of 2-[2-(2-chloroethoxy)ethoxy]ethyl difluorosulfoacetate. Yield: quantitative.

$^1$H-NMR (CDCl$_3$, Internal standard: tetramethylsilane): δ (ppm) 3.88-3.63 (12H)

MS (ESI(-) Spectrum): M$^-$ 325 (C$_8$H$_{12}$ClF$_2$O$_7$S$^-$=325.00)

(2) To 200g of chloroform, 17.8 g of sodium salt of 2-[2-(2-chloroethoxy)ethoxy]ethyl difluorosulfoacetate was added. To the obtained solution, 128.1 g of 13.1% by weight of aqueous triphenylsulfonium chloride solution was added and the resultant mixture was stirred over night. The mixture was separated to obtain the aqueous layer and the organic layer. The organic later obtained was washed with an ion-exchanged water. The organic layer was concentrated to obtain 18.0 g of the salt represented by the above-mentioned formula (C), which is called as SALT (C). Yield: 59.9%.

$^1$H-NMR (dimethylsulfoxide-d$_6$, Internal standard: tetramethylsilane): δ (ppm) 7.78-7.65 (m, 15H), 3.79-3.57 (12H)

$^{19}$F-NMR (dimethylsulfoxide-d$_6$, Internal standard: fluorobenzene): δ (ppm)-106.50

MS (ESI(+) Spectrum): M$^+$ 263 (C$_{18}$H$_{15}$S$^+$=263.09)

MS (ESI(-) Spectrum): M$^-$ 325 (C$_8$H$_{12}$ClF$_2$O$_7$S$^-$=325.00)

EXAMPLE 4

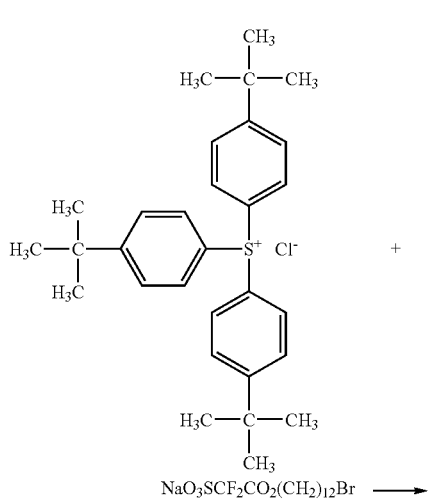

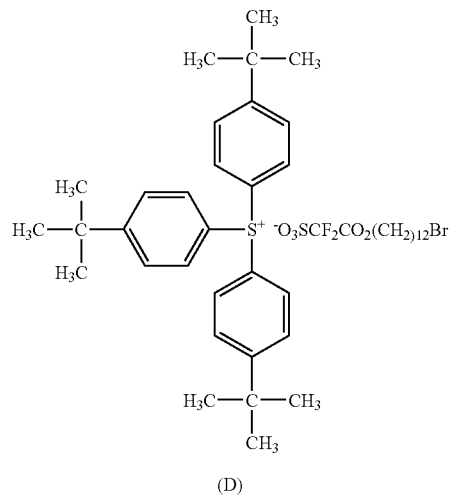

(D)

To 120g of chloroform, 20.0 g of sodium salt of 12-bromo-1-dodecyl difluorosulfoacetate was added. To the obtained solution, 210g of 10% by weight of aqueous tri(4-tert-butylphenyl)sulfonium chloride solution was added and the resultant mixture was stirred over night. The mixture was separated to obtain the aqueous layer and the organic layer. The organic later obtained was washed with an ion-exchanged water. The organic layer was concentrated to obtain 33.4 g of the salt represented by the above-mentioned formula (D), which is called as SALT (D). Yield: 87.1%.

$^1$H-NMR (CDCl$_3$, Internal standard: tetramethylsilane): δ (ppm) 7.71-7.67 (m, 12H), 4.26 (t, 2H, J=6.9 Hz), 3.41 (t, 2H, J=6.9 Hz), 1.86 (m, 2H), 1.70 (m, 2H), 1.46-1.21 (m, 16H), 1.33 (s, 27H)

$^{19}$F-NMR (dimethylsulfoxide-d$_6$, Internal standard: fluorobenzene): δ (ppm)-106.03

MS (ESI(+) Spectrum): M$^+$ 431 (C$_{30}$H$_{39}$S$^+$=431.28)

MS (ESI(-) Spectrum): M$^-$ 422, 423 (C$_{14}$H$_{24}$BrF$_2$O$_5$S$^{2-}$=421.05)

EXAMPLE 5

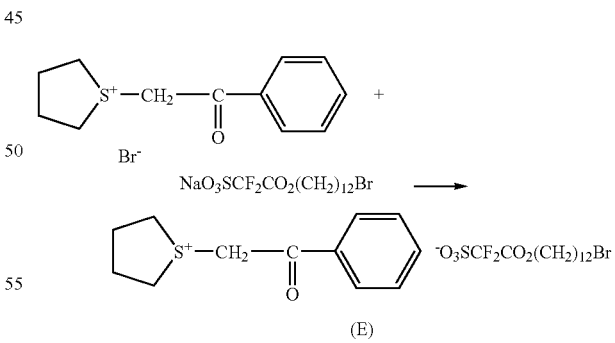

(E)

To 100g of chloroform, 15.0 g of sodium salt of 12-bromo-1-dodecyl difluorosulfoacetate was added. To the obtained solution, 9.7 g of tetrahydro-1-(2-oxo-2-phenylethyl) thiophenium bromide was added and the resultant mixture was stirred over night. To the mixture, 20 g of an ion-exchanged water was added and the resultant mixture was separated to obtain the aqueous layer and the organic layer. The organic later obtained was washed with an ion-exchanged water. The organic layer was concentrated to obtain 12.4 g of the salt represented by the above-mentioned formula (E), which is called as SALT (E). Yield: 58.5%.

$^1$H-NMR (CDCl$_3$, Internal standard: tetramethylsilane): δ (ppm) 7.99 (d, 2H, J=6.9 Hz), 7.60 (t, 1H, J=7.7 Hz), 7.45 (t, 2H, J=8.4 Hz), 5.35 (s, 2H), 4.11 (t, 2H, J=6.9 Hz), 3.75-3.70 (m, 4H), 3.64-3.59 (m, 4H), 3.41 (t, 2H, J=6.9 Hz), 2.48-2.43 (m, 4H), 2.30-2.26 (m, 4H), 1.86 (m, 2H), 1.60 (m, 2H), 1.42 (m, 2H), 1.28-1.24 (m, 14H)

$^{19}$F-NMR (dimethylsulfoxide-d$_6$, Internal standard: fluorobenzene): δ (ppm)-106.39

MS (ESI(+) Spectrum): M$^+$ 207 (C$_{12}$H$_{15}$OS$^+$=207.08)

MS (ESI(−) Spectrum): M$^−$ 422, 423 (C$_{14}$H$_{24}$BrF$_2$O$_5$S$^{2−}$=421.05)

Reference Example 1

Ten grams of 2,6-bis[4-hydroxy-3-(2-hydroxy-5-methylbenzyl)-2,5-dimethylbenzyl]-4-methylphenol (hereinafter, simply referred to as B1) was dissolved in 100 g of N,N-dimethylformamide. To the resultant solution, 6.8 g of potassium carbonate was added. To the mixture obtained, a solution obtained by mixing 7.9 g of 2-methyl-2-adamantyl chloroacetate with 40g of N,N-dimethylformamide was added dropwise below 50° C. To the mixture obtained, 0.6 g of potassium iodide was added, and the resultant mixture was stirred at 50° C. for 5 hours. The reaction mixture was cooled, diluted with 1% aqueous oxalic acid solution and then extracted with ethyl acetate. The organic layer obtained was washed with water and then, dried and decolorized using magnesium sulfate and activated carbon. The mixture obtained was filtrated and the filtrate was concentrated to obtain 15.3 g of a brown solid, which is called as A1.

A1 was analyzed by liquid chromatography to find out that three compounds represented by the following formulae (1) to (3):

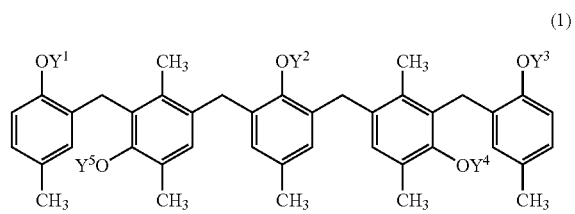

(1)

wherein any one of Y$^1$, Y$^2$, Y$^3$, Y$^4$ and Y$^5$ is the following group:

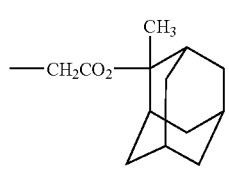

and the other four groups are hydrogen atoms (hereinafter, simply referred to as COMPOUND (1)),

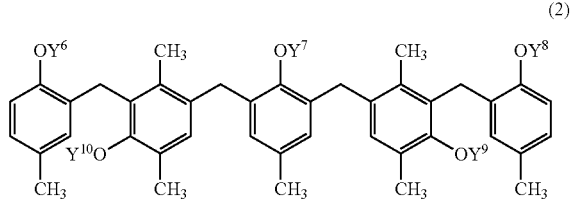

(2)

wherein any two of Y$^6$, Y$^7$, Y$^8$, Y$^9$ and Y$^{10}$ are the following groups:

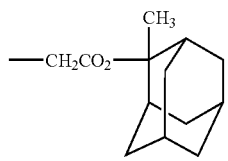

and the other three groups are hydrogen atoms (hereinafter, simply referred to as COMPOUND (2)),

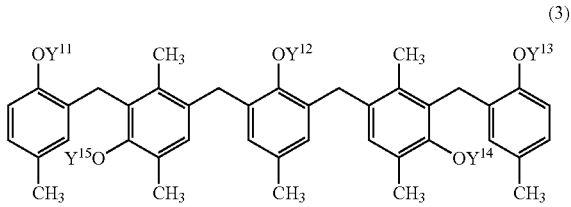

(3)

wherein any three of Y$^{11}$, Y$^{12}$, Y$^{13}$, Y$^{14}$ and Y$^{15}$ are the following groups:

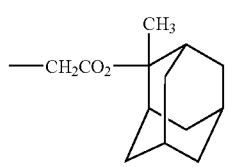

and the other two groups are hydrogen atoms (hereinafter, simply referred to as COMPOUND (3)) were contained in A1.

The content ratio of COMPOUND (1), COMPOUND (2) and COMPOUND (3) in A1 was followed. Hereinafter, "the content ratio" means a ratio of values of each compounds calculated by a liquid chromatography area percentage method.

COMPOUND (1):COMPOUND (2):COMPOUND (3)=6:92:2

Liquid chromatography mass spectroscopy;
  COMPOUND (1): [M+K]$^+$=861.4 (M$^+$=822.45)
  COMPOUND (2): [M+K]$^+$=1067.4 (M$^+$=1028.58)
  COMPOUND (3): [M+K]$^+$=1273.6 (M$^+$=1234.71)

Reference Example 2

Fifty grams of brown solid containing COMPOUND (1), COMPOUND (2) and COMPOUND (3), which was obtained according to the same manner as described in Reference Example 1, and 11.8 g of 2-methyl-2-adamantyl chloroacetate were dissolved in 150g of N,N-dimethylformamide. To the resultant solution, 10.1 g of potassium carbonate was added. To the mixture obtained, 1.6 g of potassium iodide was added, and the resultant mixture was stirred at 57 to 58° C. for 9 hours. The reaction mixture was cooled, diluted with 2% aqueous oxalic acid solution and then extracted with ethyl acetate. The organic layer obtained was washed with water and then, dried and decolorized using magnesium sulfate and activated carbon. The mixture obtained was filtrated and the filtrate was concentrated. The obtained residue was purified by silica gel chromatography (hexane/ethyl acetate) to obtain 20.0 g of a brown solid, which is called as A2.

A2 was analyzed by liquid chromatography to find out that COMPOUND (2) and COMPOUND (3) were contained in A2. COMPOUND (1) was not contained in A2.

The content ratio of COMPOUND (2) and COMPOUND (3) in A2 was followed.

COMPOUND (2):COMPOUND (3)=29:71

Reference Example 3

Three point six grams of B1 was dissolved in 36g of N,N-dimethylformamide. To the resultant solution, 0.2 g of potassium carbonate was added. To the mixture obtained, a solution obtained by mixing 3.0 g of 2-ethyl-2-adamantyl chloroacetate with 15g of N,N-dimethylformamide was added dropwise at room temperature. To the mixture obtained, 0.2 g of potassium iodide was added, and the resultant mixture was stirred at 50° C. for 5 hours. The reaction mixture was cooled, diluted with 5% aqueous oxalic acid solution and then extracted with ethyl acetate. The organic layer obtained was washed with water and then, dried and decolorized using magnesium sulfate and activated carbon. The mixture obtained was filtrated and the filtrate was concentrated to obtain 3.41 g of a brown solid, which is called as A3.

A3 was analyzed by liquid chromatography to find out that three compounds represented by the following formulae (4) to (6):

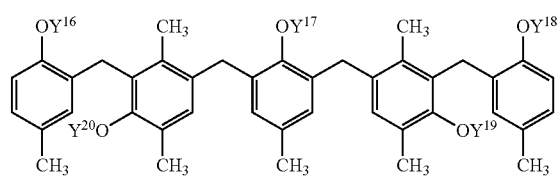

(4)

wherein any one of $Y^{16}, Y^{17}, Y^{18}, Y^{19}$ and $Y^{20}$ is the following group:

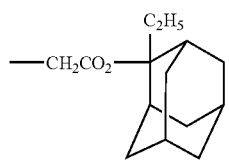

and the other four groups are hydrogen atoms (hereinafter, simply referred to as COMPOUND (4)),

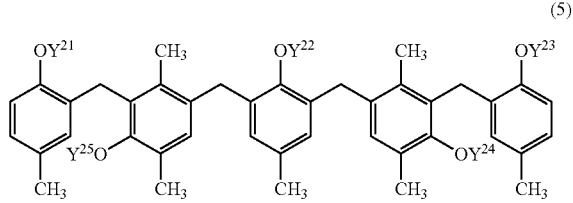

(5)

wherein any two of $Y^{21}, Y^{22}, Y^{23}, Y^{24}$ and $Y^{25}$ are the following groups:

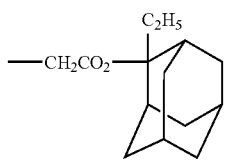

and the other three groups are hydrogen atoms (hereinafter, simply referred to as COMPOUND (5)),

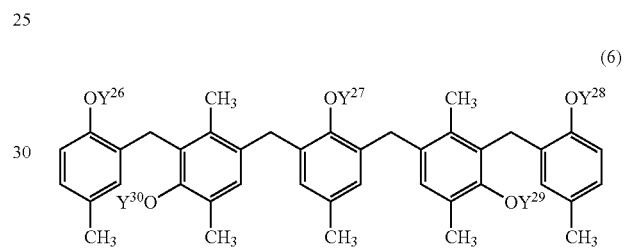

(6)

wherein any three of $Y^{26}, Y^{27}, Y^{28}, Y^{29}$ and $Y^{30}$ are the following groups:

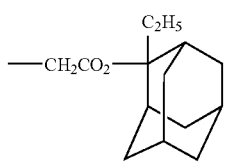

and the other two groups are hydrogen atoms (hereinafter, simply referred to as COMPOUND (6)) were contained in A3.

The content ratio of COMPOUND (4), COMPOUND (5) and COMPOUND (6) in A3 was followed.

COMPOUND (4):COMPOUND (5):COMPOUND (6)=12:84:4

Liquid chromatography mass spectroscopy;
COMPOUND (4): [M+K]"=875.5 (M"=836.47)
COMPOUND (5): [M+K]"=1095.4 (M"=1056.61)
COMPOUND (6): [M+K]"=1315.5 (M"=1276.76)

EXAMPLE 6

A mixture obtained by mixing 7.5g of A1 obtained in Reference Example 1, 5.0 g of SALT (A), 1.5 g of potassium carbonate and 60g of acetone was refluxed for 4 hours. The resultant mixture was cooled and diluted and neutralized with 2% aqueous oxalic acid solution. The obtained mixture was extracted with ethyl acetate. The organic layer obtained was washed with ion-exchanged water and concentrated to obtain 8.9 g of a composition containing a compound represented by the formula (7):

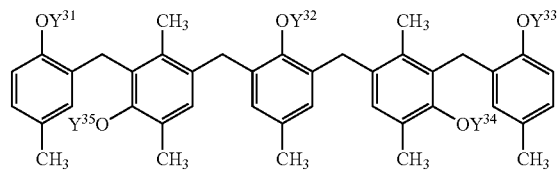

(7)

wherein any two of $Y^{31}, Y^{32}, Y^{33}, Y^{34}$ and $Y^{35}$ are the following groups:

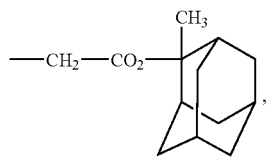

and the other one group is the following group:

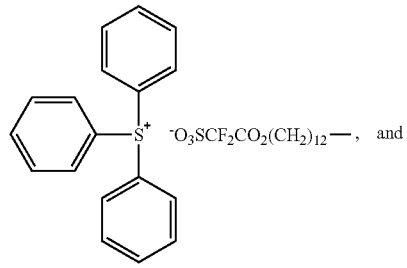, and the other two groups are hydrogen atoms, as a main component. The composition obtained is called as P1. Yield: 75.2%.

MS (ESI(+) Spectrum): M⁺ 263 (C18H$_{15}$S⁺=263.09)

MS (ESI(−) Spectrum): M⁻ 1369 ($C_{81}H_{103}F_2O_{14}S^-$=1369.70)

EXAMPLE 7

A mixture obtained by mixing 4.6 g of B1, 10.3 g of SALT (A), 3.1 g of potassium carbonate and 60 g of acetone was refluxed for 3 hours. The resultant mixture was cooled and diluted and neutralized with 2% aqueous oxalic acid solution. The obtained mixture was extracted with ethyl acetate. The organic layer obtained was washed with an ion-exchanged water and concentrated to obtain 11.8 g of a composition containing a compound represented by the formula (8):

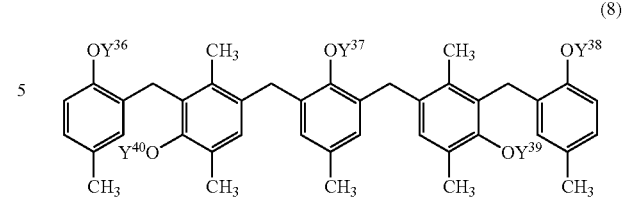

(8)

wherein any two of $Y^{36}, Y^{37}, Y^{38}, Y^{39}$ and $Y^{40}$ are the following groups:

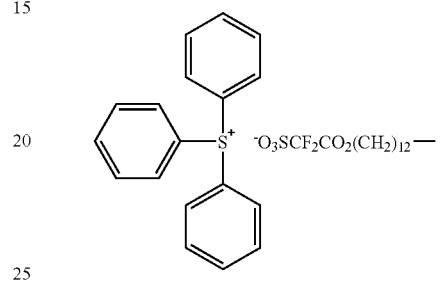

and the other three groups are hydrogen atom, as a main component. The composition obtained is called as P2. Yield: 86.6%.

MS (ESI(+) Spectrum): M⁺ 263 ($C_{18}H_{15}S^+$=263.09)

MS (ESI(−) Spectrum): M⁻ 1298 ($C_{69}H_{90}F_4O_{15}S_2^-$=1298.57)

EXAMPLE 8

According to the same manner as described in Reference Example 3, a brown solid was obtained, which is called as A3'

A3' was analyzed by liquid chromatography to find out that three compounds, COMPOUND (4), COMPOUND (5) and COMPOUND (6), were contained in A3', and the content ratio of COMPOUND (4), COMPOUND (5) and COMPOUND (6) in A3' was followed.

COMPOUND (4):COMPOUND (5):COMPOUND (6)=12:85:3

A mixture obtained by mixing 10.0 g of A3', 6.5 g of SALT (A), 1.6 g of potassium carbonate and 60g of acetone was refluxed for 4 hours. The resultant mixture was cooled and diluted and neutralized with 2% aqueous oxalic acid solution. The obtained mixture was extracted with ethyl acetate. The organic layer obtained was washed with an ion-exchanged water and concentrated to obtain 13.0 g of a composition containing a compound represented by the formula (9):

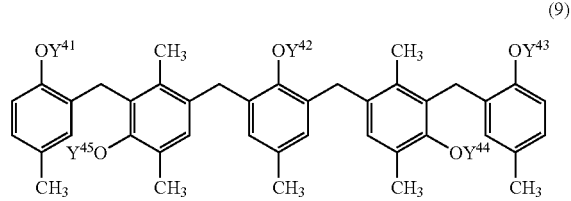

(9)

wherein any two of $Y^{41}, Y^{42}, Y^{43}, Y^{44}$ and $Y^{45}$ are the following groups:

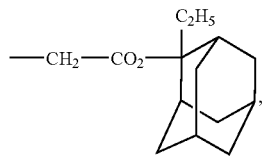

the other one is the following group:

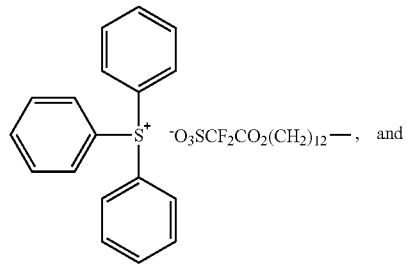

the other two groups are hydrogen atoms, as a main component. The composition obtained is called as P3. Yield: 82.7%.

MS (ESI(+) Spectrum): $M^+$ 263 ($C_{18}H_{15}S^+$=263.09)
MS (ESI(−) Spectrum): $M^−$ 1397 ($C_{83}H_{107}F_2O_{14}S^−$=1397.73)

Reference Example 4

Ten grams of B1 was dissolved in 100g of N,N-dimethylformamide. To the resultant solution, 3.4 g of potassium carbonate was added. To the mixture obtained, a solution obtained by mixing 4.0 g of 2-methyl-2-adamantyl chloroacetate with 40g of N,N-dimethylformamide was added dropwise below 50° C. To the mixture obtained, 0.3 g of potassium iodide was added, and the resultant mixture was stirred at 50° C. for 5 hours. The reaction mixture was cooled, diluted with 1% aqueous oxalic acid solution and then extracted with ethyl acetate. The organic layer obtained was washed with water and then, dried and decolorized using magnesium sulfate and activated carbon. The mixture obtained was filtrated and the filtrate was concentrated to obtain 7.6 g of a brown solid.

The same procedure as described above was repeated twice.

The obtained brown solids were mixed to obtain 25.0 g of a brown solid.

The obtained brown solid was analyzed by liquid chromatography to find out that three compounds, B1, COMPOUND (1) and COMPOUND (2), were contained in the obtained brown solid. COMPOUND (3) was not contained in the obtained brown solid.

The obtained brown solid was purified with silica gel chromatography using 100 g of silica gel and a mixed solvent of hexane and ethyl acetate to obtain a solid, which is called as A4.

A4 was analyzed by liquid chromatography to find out that two compounds, COMPOUND (1) and COMPOUND (2), were contained in A4.

The content ratio of COMPOUND (1) and COMPOUND (2) in A4 was followed.

COMPOUND (1):COMPOUND (2)=96:4

EXAMPLE 9

A mixture obtained by mixing 5.0 g of A4, 5.2 g of SALT (D), 1.0 g of potassium carbonate and 40 g of acetone was refluxed for 3 hours. The resultant mixture was cooled and pH thereof was adjusted to 3 with 2% aqueous oxalic acid solution. The obtained mixture was extracted with ethyl acetate. The organic layer obtained was washed with ion-exchanged water and concentrated to obtain 8.9 g of a composition containing a compound represented by the formula (10):

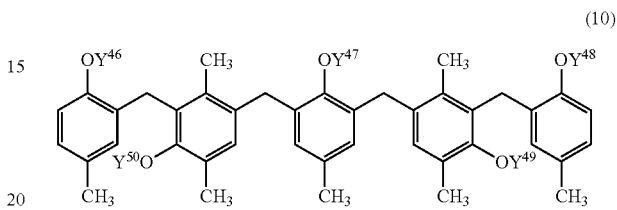

(10)

wherein any one of $Y^{46}, Y^{47}, Y^{48}, Y^{49}$ and $Y^{50}$ is the following group:

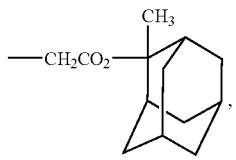

the other one group is the following group:

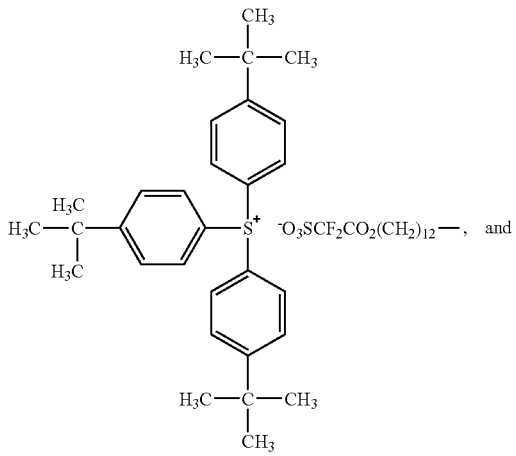

the other three groups are hydrogen atoms, as a main component. The composition obtained is called as P4. Yield: 69.6%.

MS (ESI(+) Spectrum): $M^+$ 431 ($C_{30}H_{39}S^+$=431.28)
MS (ESI(−) Spectrum): $M^−$ 1164 ($C_{68}H_{88}F_2O_{12}S^−$=1164.46)

Reference Example 5

Ten grams of B1 was dissolved in 100 g of N,N-dimethylformamide. To the resultant solution, 6.1 g of potassium carbonate was added. To the mixture obtained, a solution obtained by mixing 7.1 g of 2-methyl-2-adamantyl chloroacetate with 40 g of N,N-dimethylformamide was added dropwise below 50° C. To the mixture obtained, 0.5 g of potassium iodide was added, and the resultant mixture was stirred at 50° C. for 5 hours. The reaction mixture was cooled, diluted with 1% aqueous oxalic acid solution and then extracted with ethyl acetate. The organic layer obtained was washed with water and then, dried and decolorized using magnesium sulfate and activated carbon. The mixture obtained was filtrated and the filtrate was concentrated to obtain 12.5 g of a brown solid, which is called as A5.

A5 was analyzed by liquid chromatography to find out that three compounds, B1, COMPOUND (1) and COMPOUND (2), were contained in A5. COMPOUND (3) was not contained in A5.

The content ratio of B1, COMPOUND (1) and COMPOUND (2) in A5 was followed.

B1:COMPOUND (1):COMPOUND (2)=1:21:78

EXAMPLE 10

A mixture obtained by mixing 5.0 g of A5, 3.0 g of SALT (B), 0.8 g of potassium carbonate and 40g of acetone was refluxed for 3 hours. The resultant mixture was cooled and pH thereof was adjusted to 3 with 2% aqueous oxalic acid solution. The obtained mixture was extracted with ethyl acetate. The organic layer obtained was washed with ion-exchanged water and concentrated to obtain 5.22 g of a composition containing a compound represented by the formula (11):

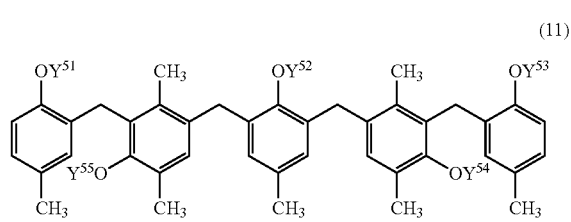

(11)

wherein any two of $Y^{51}$, $P^{52}$, $Y^{53}$, $Y^{54}$ and $Y^{55}$ are the following groups:

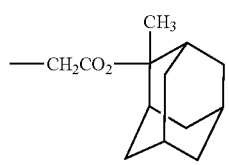

and the other one is the following group:

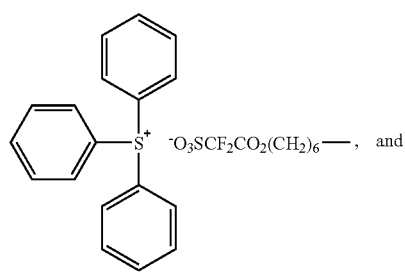

the other two groups are hydrogen atoms, as a main component. The composition obtained is called as P5. Yield: 69.3%.

MS (ESI(+) Spectrum): M⁺ 263 ($C_{18}H_{15}S^+$=263.09)

MS (ESI(−) Spectrum): M⁻ 1271 ($C_{74}H_{89}F_2O_{14}S^-$=1271.59)

EXAMPLE 11

A mixture obtained by mixing 5.0 g of A3', 3.1 g of SALT (E), 0.81 g of potassium carbonate and 40g of acetone was refluxed for 3 hours. The resultant mixture was cooled and diluted and pH thereof was adjusted to 3 with 2% aqueous oxalic acid solution. The obtained mixture was extracted with ethyl acetate. The organic layer obtained was washed with ion-exchanged water and concentrated to obtain 5.18 g of a composition containing a compound represented by the formula (12):

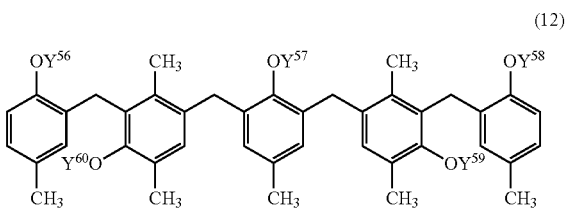

(12)

wherein any two of $Y^{56}$, $Y^{57}$, $Y^{58}$, $Y^{59}$ and $Y^{60}$ are the following groups:

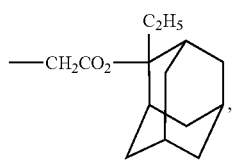

the other one is the following group:

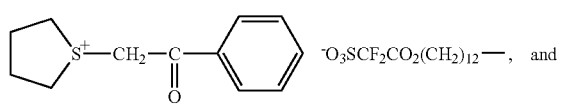

the other two groups are hydrogen atoms, as a main component. The composition obtained is called as P6. Yield: 68.2%.

MS (ESI(+) Spectrum): M⁺ 207 ($C_{12}H_{15}OS^+$=207.08)

MS (ESI(−) Spectrum): M⁻ 1397 ($C_{83}H_{107}F_2O_{14}S^-$=1397.73)

Reference Example 6

According to the method described in JP 2003-107708 A1, a copolymer of 2-ethyl-2-adamantyl methacrylate and p-hydroxystyrene (2-ethyl-2-adamantyl methacrylate/p-hydroxystyrene ratio=20/80), which is called as C1, and a copolymer of 2-ethyl-2-adamantyl methacrylate and p-hydroxystyrene (2-ethyl-2-adamantyl methacrylate/p-hydroxystyrene ratio=30/70), which is called as C2, were synthesized.

Reference Example 7

According to the method described in U.S. Pat. No. 5,556, 995 B1, the compound represented by the following formula:

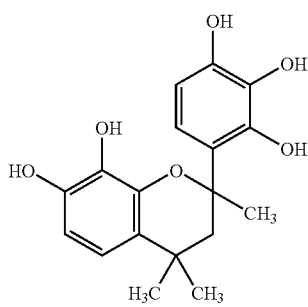

was synthesized from pyrogallol and acetone, which is called as B2.

Acid generators, quenchers and solvents used in following Examples are followings.

<Acid Generator>
Acid generator S1: (4-methylphenyl)diphenylsulfonium nonafluorobutanesulfonate
<Quencher>
Quencher $Q_a$: 2,6-diisopropylaniline
Quencher $Q_b$: tetrabutylammonium hydroxide
<Solvent>
Solvent Y: propylene glycol monomethyl ether acetate Examples 12 to 19 and Comparative Examples 1 to 3

The following components were mixed to give a solution, and the solution was further filtrated through a fluorine resin filter having a pore diameter of 0.2 μm, to prepare resist liquid.
Compound (kind and amount are described in Table 1)
Acid generator (kind and amount are described in Table 1)
Quencher (kind and amount are described in Table 1)
Solvent (kind are described in Table 1)

TABLE 1

| Ex. No. | Compound (kind/amount (part)) | Acid generator (kind/amount (part)) | Quencher (kind/amount (part)) | Solvent (kind/amount (part)) | PB (° C.) | PEB (° C.) |
|---|---|---|---|---|---|---|
| Ex. 12 | P1/3 A1/5 B1/2 | None | $Q_a$/0.2 $Q_b$/0.05 | Y/320 | 110 | 100 |
| Ex. 13 | P1/4 A1/4 B1/2 | None | $Q_a$/0.2 $Q_b$/0.05 | Y/320 | 110 | 100 |
| Ex. 14 | P1/4 A1/5 B1/1 B2/1 | None | $Q_a$/0.2 $Q_b$/0.05 | Y/320 | 110 | 100 |
| Ex. 15 | P1/5 A3/3 B1/2 | None | $Q_a$/0.2 $Q_b$/0.05 | Y/320 | 110 | 100 |
| Ex. 16 | P1/4 A3/4 B1/2 | None | $Q_a$/0.2 $Q_b$/0.05 | Y/320 | 110 | 100 |
| Ex. 17 | P1/3 A3/5 B1/2 | None | $Q_a$/0.2 $Q_b$/0.05 | Y/320 | 110 | 100 |
| Ex. 18 | P3/5 A3/3 B1/2 | None | $Q_a$/0.2 $Q_b$/0.05 | Y/220 | 110 | 90 |
| Ex. 19 | P3/4 A3/4 B1/2 | None | $Q_a$/0.2 $Q_b$/0.05 | Y/220 | 110 | 90 |
| Comp. Ex. 1 | C1/5 C2/5 | S1/1 | $Q_a$/0.01 $Q_b$/0.01 | Y/320 | 110 | 100 |
| Comp. Ex. 2 | C1/5 C2/5 | S1/1 | $Q_a$/0.05 | Y/320 | 110 | 100 |
| Comp. Ex. 3 | C1/5 C2/5 | S1/3 | $Q_a$/0.2 $Q_b$/0.05 | Y/320 | 110 | 100 |

Silicon wafers were each contacted with hexamethyldisilazane at a temperature shown in the column of "PB" in Table 1 for 60 seconds and each of the resist liquids prepared as above was spin-coated over the silicon wafer to give a film thickness after drying of 0.10 μm. After application of each of the resist liquids, the silicon wafers thus coated with the respective resist liquids were each prebaked on a direct hotplate at a temperature shown in the column of "PB" in Table 1 for 60 seconds. Using a writing electron beam lithography system ("HL-800D" manufactured by Hitachi, Ltd., 50 KeV), each wafer on which the respective resist film had been thus formed was exposed to a line and space pattern, while changing stepwise the exposure quantity.

After the exposure, each wafer was subjected to post-exposure baking on a hotplate at a temperature shown in the column of "PEB" in Table 1 for 60 seconds and then to paddle development with an aqueous solution of 2.38% by weight tetramethylammonium hydroxide for 60 seconds.

Each of a pattern developed on the silicon substrate after the development was observed with a scanning electron microscope, and the results of which are shown in Table 2.

Effective Sensitivity (ES): It is expressed as the amount of exposure that the line pattern and the space pattern become 1:1 after exposure through 0.10 μm line and space pattern mask and development.

Resolution: It is expressed as the minimum size of space pattern which gave the space pattern split by the line pattern at the exposure amount of the effective sensitivity.

Line Edge Roughness (LER): LER was of 1:1 line and space pattern of 0.12 μm was observed with a scanning electron microscope from upper side. When LER is good, its evaluation is marked by "○", and when LER is bad, its evaluation is marked by "X".

TABLE 2

| Ex. No. | ES (μC) | Resolution (nm) | LER |
|---|---|---|---|
| Ex. 12 | 18 | 70 | ○ |
| Ex. 13 | 22 | 70 | ○ |
| Ex. 14 | 28 | 70 | ○ |
| Ex. 15 | 16 | 70 | ○ |
| Ex. 16 | 20 | 70 | ○ |
| Ex. 17 | 26 | 60 | ○ |
| Ex. 18 | 24 | 60 | ○ |
| Ex. 19 | 32 | 60 | ○ |
| Comp. Ex. 1 | 14 | 90 | X |
| Comp. Ex. 2 | 28 | 70 | X |
| Comp. Ex. 3 | 48 | 60 | ○ |

Apparent from the results shown in Table 2, resist compositions obtained by Examples corresponding to the present invention show good sensitivity, resolution and line edge roughness.

EXAMPLE 20

A resist pattern can be obtained according to the same manner as described in Example 12, except that P1 and P3 are used in place of P1.

EXAMPLE 21

A resist pattern can be obtained according to the same manner as described in Example 12, except that P4 is used in place of P1.

EXAMPLE 22

A resist pattern can be obtained according to the same manner as described in Example 12, except that P5 is used in place of P1.

EXAMPLE 23

A resist pattern can be obtained according to the same manner as described in Example 12, except that P6 is used in place of P1.

EXAMPLE 24

A resist pattern was obtained according to the same manner as described in Example 19, except that 4 parts of P2 was used in place of 4 parts of P3 and the following Solvent $Y^1$ was used in place of 220 parts of Solvent Y. The result is shown in Table 3.

Solvent $Y^1$:

| | |
|---|---|
| propylene glycol monomethyl ether acetate | 160 parts |
| propylene glycol monomethyl ether | 100 parts |
| γ-butyrolactone | 5 parts |

EXAMPLE 25

A resist pattern was obtained according to the same manner as described in Example 19, except that 2 parts of P1 and 2 parts of P2 were used in place of 4 parts of P3 and the above-mentioned Solvent $Y^1$ was used in place of 220 parts of Solvent Y. The result is shown in Table 3.

TABLE 3

| Ex. No. | ES (μC) | Resolution (nm) | LER |
|---|---|---|---|
| Ex. 24 | 32 | 70 | ○ |
| Ex. 25 | 32 | 60 | ○ |

The present resist composition provides excellent resist pattern in line edge roughness and is suitable for ArF excimer laser lithography, extreme ultraviolet (EUV) lithography and electron lithography.

What is claimed is:

1. A polyhydric compound represented by the formula (I):

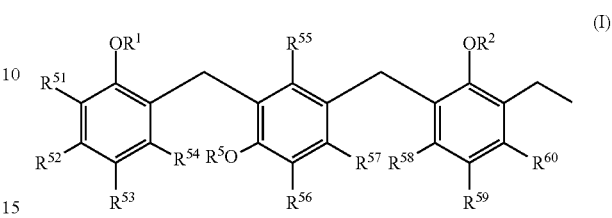

(I)

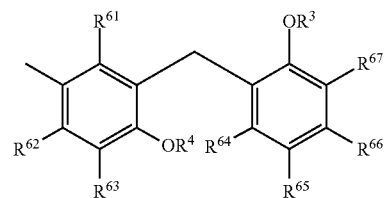

wherein $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$ and $R^{67}$ each independently represent a hydrogen atom or a C1-C4 alkyl group, at least one selected from the group consisting of $R^1$, $R^2$, $R^3$, $R^4$ and $R^5$ is a group represented by the formula (II):

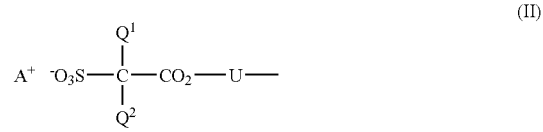

(II)

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, and $A^+$ represents an organic counter ion, and the others are hydrogen atoms or groups represented by the formula (III):

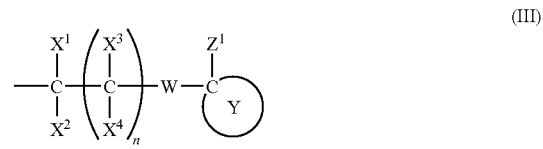

(III)

wherein $X^1$, $X^2$, $X^3$ and $X^4$ each independently represent a hydrogen atom or a C1-C4 alkyl group, n represents an integer of 0 to 3, W represents any one of the following groups:

—CO—O—, —O—CH$_2$—O—,

—O—CH$_2$—O—CO—, —O—CH(CH$_3$)—O—,

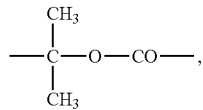

$Z^1$ represents a C1-C6 alkyl group or a C3-C12 cycloalkyl group, provided that when W is not —CO—O—, $Z^1$ may be a hydrogen atom, and ring Y represents a C3-C20 alicyclic hydrocarbon group.

2. The polyhydric compound according to claim 1, wherein at least one selected from the group consisting of $R^1$, $R^2$, $R^3$, $R^4$ and $R^5$ is a group represented by the formula (III).

3. The polyhydric compound according to claim 1 or 2, wherein $X^1$ and $X^2$ represent hydrogen atoms, n represents 0 and W is —CO—O—.

4. The polyhydric compound according to claim 1, wherein $Q^1$ and $Q^2$ are fluorine atoms.

5. The polyhydric compound according to claim 1, wherein the organic counter ion is at least one cation selected from the group consisting of a cation represented by the formula (VIa):

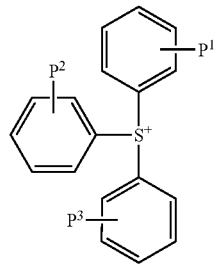

(VIa)

wherein $P^1$, $P^2$ and $P^3$ each independently represent a hydrogen atom, a hydroxyl group, a C1-C12 alkyl group or a C1-C12 alkoxy group, a cation represented by the formula (VIb):

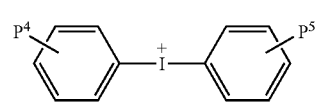

(VIb)

wherein $P^4$ and $P^5$ each independently represent a hydrogen atom, a hydroxyl group, a C1-C12 alkyl group or a C1-C12 alkoxy group, and a cation represented by the forula (VIc):

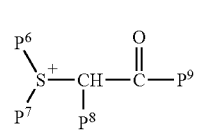

(VIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —CH$_2$— in the divalent acyclic hydrocarbon group is optionally replaced with —CO—, —O— or —S—, $P^8$ represents a hydrogen atom, $P^9$ represents a C1-C12 alkyl group, a C3-C12 cycloalkyl group or a C6-C10 aromatic group which may be substituted, or $P^8$ and $P^9$ are bonded to form a divalent hydrocarbon group which forms a 2-oxocycloalkyl group together with the adjacent —CHCO—, and at least one —CH$_2$— in the divalent hydrocarbon group may be replaced with —CO—, —O— or —S—.

6. The polyhydric compound according to claim 1, wherein the molecular weight of the polyhydric compound represented by the formula (I) is 500 to 5,000.

7. A chemically amplified resist composition comprising: a polyhydric compound represented by the formula (I):

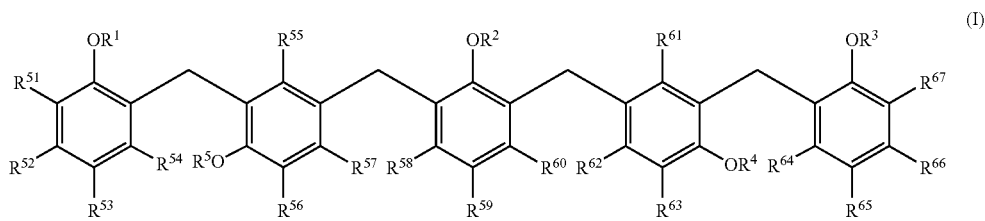

(I)

wherein $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$ and $R^{67}$ each independently represent a hydrogen atom or a C1-C4 alkyl group, at least one selected from the group consisting of $R^1$, $R^2$, $R^3$, $R^4$ and $R^5$ is a group represented by the formula (II):

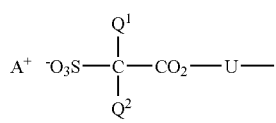

(II)

wherein $Q^1$ and $Q^2$ each independently represent a fluorine atom or a C1-C6 perfluoroalkyl group, U represents a C1-C20 divalent hydrocarbon group and $A^+$ represents an organic counter ion, and the others are hydrogen atoms or groups represented by the formula (III):

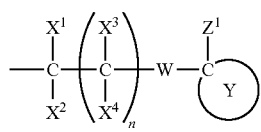

(III)

wherein $X^1$, $X^2$, $X^3$ and $X^4$ each independently represent a hydrogen atom or a C1-C4 alkyl group, n represents an integer of 0 to 3, W represents any one of the following groups:

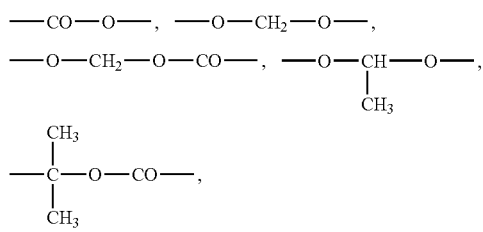

$Z^1$ represents a C1-C6 alkyl group or a C3-C12 cycloalkyl group, provided that when W is not —CO—O—, $Z^1$ may be a hydrogen atom, and ring Y represents a C3-C20 alicyclic hydrocarbon group, and a solvent.

8. The composition according to claim 7, wherein the composition further comprises at least one selected from the group consisting of a compound represented by the formula (I'-1):

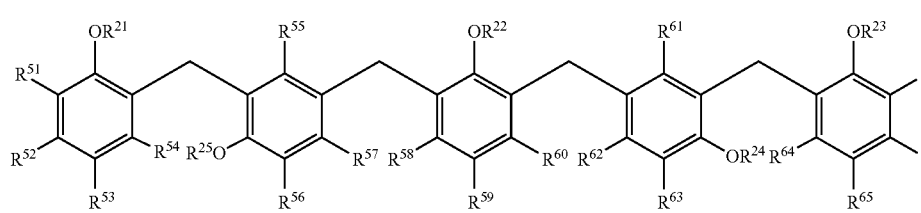

(I'-1)

wherein $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$ $R^{64}$, $R^{65}$, $R^{66}$ and $R^{67}$ each independently represent a hydrogen atom or a C1-C4 alkyl group, and at least one selected from the group consisting of $R^{21}$, $R^{22}$, $R^{23}$, $R^{24}$ and $R^{25}$ is a group represented by the formula (III):

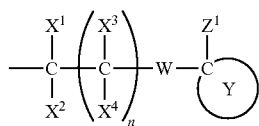

(III)

wherein $X^1$, $X^2$, $X^3$ and $X^4$ each independently represent a hydrogen atom or a C1-C4 alkyl group, n represents an integer of 0 to 3, W represents any one of the following groups:

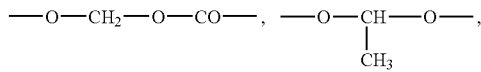

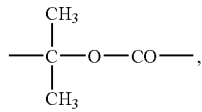

$Z^1$ represents a C1-C6 alkyl group or a C3-C12 cycloalkyl group, provided that when W is not —CO—O—, $Z^1$ may be a hydrogen atom, and ring Y represents a C3-C20 alicyclic hydrocarbon group, and the others are hydrogen atoms, a compound represented by the formula (I'-2):

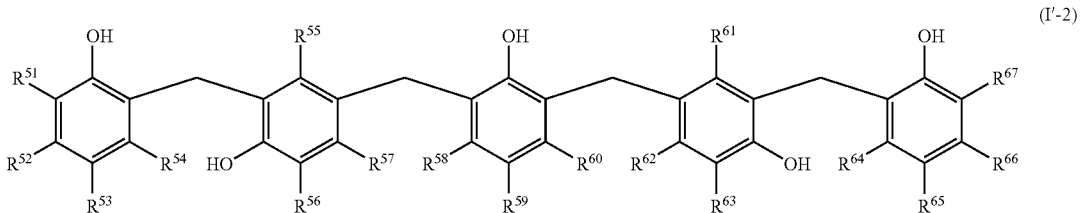

wherein $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$ and $R^{67}$ are the same as defined above, a compound represented by the formula (I'-3):

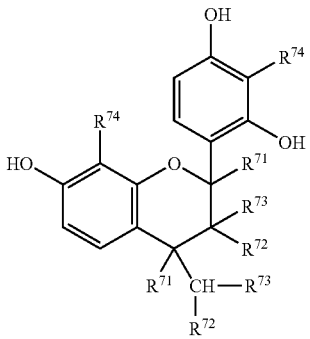

wherein $R^{71}$, $R^{72}$ and $R^{73}$ each independently represent a hydrogen atom, a C1-C4 alkyl group, a C2-C4 alkenyl group, a C3-C8 cycloalkyl group, a C6-C12 aryl group or a C7-C12 aralkyl group, and $R^{74}$ represents a hydrogen atom or a hydroxyl group, and a compound represented by the formula (I'-4):

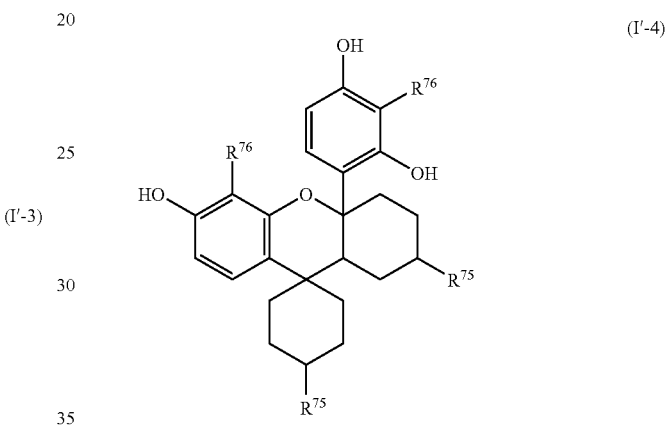

wherein $R^{75}$ represents a hydrogen atom, a C1-C4 alkyl group, a C2-C4 alkenyl group, a C3-C8 cycloalkyl group, a C6-C12 aryl group or a C7-C12 aralkyl group, and $R^{76}$ represents a hydrogen atom or a methyl group.

9. The composition according to claim 7, wherein the composition further comprises compounds represented by the formulae (I'-1) and (I'-2).

10. The composition according to claim 7, wherein the composition further comprises compounds represented by the formulae (I'-1), (I'-2) and (I'-3).

11. The composition according to claim 7, wherein the composition comprises two or more kinds of a polyhydric compound represented by the formula (I).

12. A process for producing a polyhydric compound represented by the formula (I):

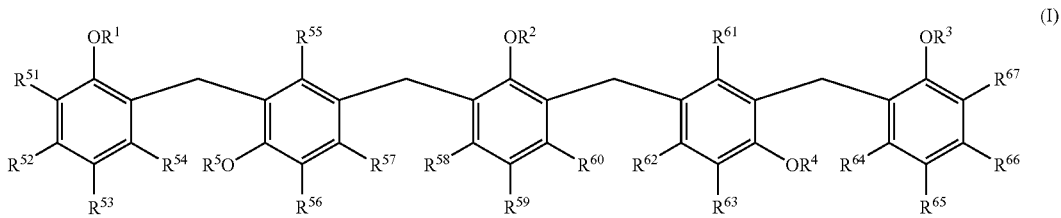

wherein $R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}$ and $R^{67}$ each independently represent a hydrogen atom or a C1-C4 alkyl group, at least one selected from the group consisting of $R^1$, $R^2$, $R^3$, $R^4$ and $R^5$ is a group represented by the formula (II):

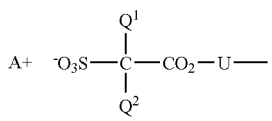

(II)

wherein $Q^1$ and $Q^2$ each independently represent a fluorine atom or a C1-C6 perfluoroalkyl group, U represents a C1-C20 divalent hydrocarbon group and $A^+$ represents an organic counter ion, and the others are hydrogen atoms or groups represented by the formula (III):

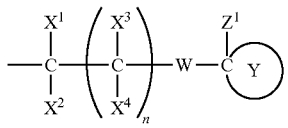

(III)

wherein $X^1$, $X^2$, $X^3$ and $X^4$ each independently represent a hydrogen atom or a C1-C4 alkyl group, n represents an integer of 0 to 3, W represents any one of the following groups:

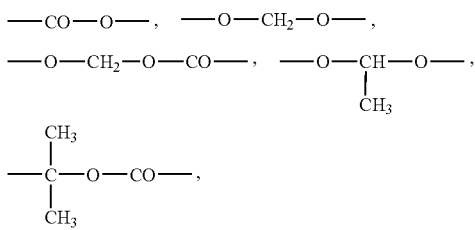

$Z^1$ represents a C1-C6 alkyl group or a C3-C12 cycloalkyl group, provided that when W is not —CO—O—, $Z^1$ may be a hydrogen atom, and ring Y represents a C3-C20 alicyclic hydrocarbon group, which comprises reacting a compound represented by the formula (VII):

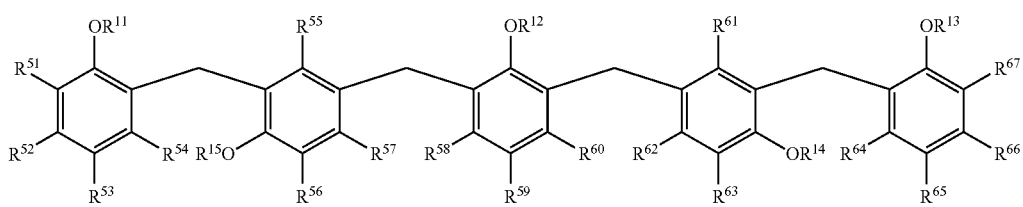

(VII)

wherein $R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}$ and $R^{67}$ are the same as defined above, at least one selected from the group consisting of $R^{11}$, $R^{12}$, $R^{13}$, $R^{14}$ and $R^{15}$ is a hydrogen atom and the others are hydrogen atoms or groups represented by the above-mentioned formula (III) with a compound represented by the formula (VIII):

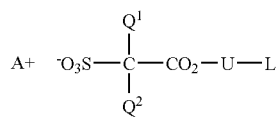

(VIII)

wherein $Q^1$, $Q^2$, U and $A^+$ are the same as defined above and L represents a halogen atom, a C1-C12 alkylsulfonyloxy group or a C6-C12 arylsulfonyloxy group wherein at least one carbon atom of the aryl group may be replaced with a hetero atom, in the presence of a base.

13. A compound represented by the formula (VIII):

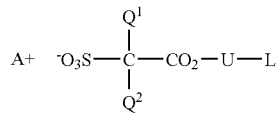

(VIII)

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, $A^+$ represents an organic counter ion, and L represents a halogen atom, a C1-C12 alkylsulfonyloxy group or a C6-C12 arylsulfonyloxy group wherein at least one carbon atom of the aryl group may be replaced with a hetero atom.

14. A process for producing a compound represented by the formula (VIII):

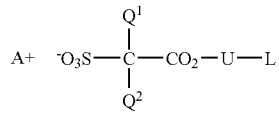

(VIII)

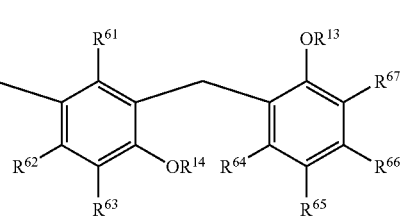

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, $A^+$ represents an organic counter ion, and L represents a halogen atom, a C1-C12 alkylsulfonyloxy group or a C6-C12 arylsulfonyloxy group wherein at least one carbon atom of the aryl group may be replaced with a hetero atom, which comprises reacting a compound represented by the formula (X):

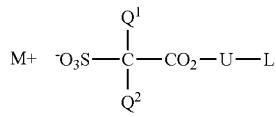  (X)

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, $M^+$ represents $Li^+$, $Na^+$, $K^+$ or $Ag^+$, and L represents a halogen atom, a C1-C12 alkylsulfonyloxy group or a C6-C12 arylsulfonyloxy group wherein at least one carbon atom of the aryl group may be replaced with a hetero atom, with a compound represented by the formula (XI):

$A^+Z^-$  (XI)

wherein $A^+$ is the same as defined above and $Z^-$ represents $F^-$, $Cl^-$, $Br^-$, $I^-$, $BF_4^-$, $AsF_6^-$, $SbF_6^-$, $PF_6^-$ or $ClO_4^-$.

15. A compound represented by the formula (X):

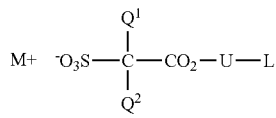  (X)

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, $M^+$ represents $Li^+$, $Na^+$, $K^+$ or $Ag^+$, and L represents a halogen atom, a C1-C12 alkylsulfonyloxy group or a C6-C12 arylsulfonyloxy group wherein at least one carbon atom of the aryl group may be replaced with a hetero atom.

16. A process for producing a compound represented by the formula (X):

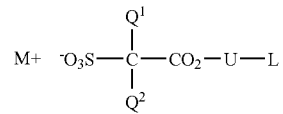  (X)

wherein $Q^1$ and $Q^2$ each independently represent a fluorine atom or a C1-C6 perfluoroalkyl group, U represents a C1-C20 divalent hydrocarbon group of which at least one methylene group may be replaced with —O—, —S—, —NH—, —CO—, —CO—O— or —NR— wherein R represents an alkyl group, $M^+$ represents $Li^+$, $Na^+$, $K^+$ or $Ag^+$, and L represents a halogen atom, a C1-C12 alkylsulfonyloxy group or a C6-C12 arylsulfonyloxy group wherein at least one carbon atom of the aryl group may be replaced with a hetero atom, which comprises reacting an alcohol compound represented by the formula (XII):

HO—U-L  (XII)

wherein U and L are the same as defined above, with a carboxylic acid represented by the formula (XIII):

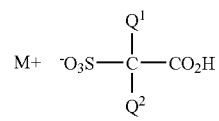  (XIII)

wherein $Q^1$, $Q^2$ and $M^+$ are the same as defined above.

* * * * *